(12) United States Patent
DeGrado et al.

(10) Patent No.: US 8,987,306 B2
(45) Date of Patent: *Mar. 24, 2015

(54) INHIBITORS OF INTEGRIN ALPHA2BETA1 BASED ON PROLYL DIAMINOPROPIONIC ACID SCAFFOLD

(75) Inventors: William F. DeGrado, San Francisco, CA (US); Meredith W. Miller, Philadelphia, PA (US); Sandeep Basra, Munich (DE); Joel S. Bennett, Bryn Mawr, PA (US); Sungwook Choi, San Diego, CA (US)

(73) Assignee: The Trustees Of The University of Pennsylvania, Philadelphia, PA (US)

( * ) Notice: Subject to any disclaimer, the term of this patent is extended or adjusted under 35 U.S.C. 154(b) by 1084 days.

This patent is subject to a terminal disclaimer.

(21) Appl. No.: 12/566,162

(22) Filed: Sep. 24, 2009

(65) Prior Publication Data

US 2010/0179119 A1    Jul. 15, 2010

Related U.S. Application Data

(63) Continuation-in-part of application No. 12/237,015, filed on Sep. 24, 2008, now Pat. No. 7,910,609, which is a continuation of application No. 11/916,746, filed as application No. PCT/US2006/022225 on Jun. 7, 2006, now Pat. No. 8,258,159.

(60) Provisional application No. 61/099,747, filed on Sep. 24, 2008, provisional application No. 60/687,972, filed on Jun. 7, 2005.

(51) Int. Cl.
*A01N 43/40* (2006.01)
*A61K 31/445* (2006.01)
*A01N 43/78* (2006.01)
*A61K 31/425* (2006.01)
*A01N 43/36* (2006.01)
*A61K 31/40* (2006.01)
*C07D 211/22* (2006.01)
*C07D 277/00* (2006.01)
*C07D 207/48* (2006.01)
*C07D 205/04* (2006.01)
*C07D 211/96* (2006.01)
*C07D 215/58* (2006.01)
*C07D 217/26* (2006.01)
*C07D 277/06* (2006.01)
*C07K 5/078* (2006.01)
*A61K 38/00* (2006.01)

(52) U.S. Cl.
CPC ............ *C07D 207/48* (2013.01); *C07D 205/04* (2013.01); *C07D 211/96* (2013.01); *C07D 215/58* (2013.01); *C07D 217/26* (2013.01); *C07D 277/06* (2013.01); *C07K 5/06165* (2013.01); *A61K 38/00* (2013.01)
USPC ........... 514/327; 514/369; 514/423; 546/221; 548/188

(58) Field of Classification Search
None
See application file for complete search history.

(56) References Cited

U.S. PATENT DOCUMENTS

| | | |
|---|---|---|
| 6,096,707 A | 8/2000 | Heino et al. |
| 6,369,034 B1 | 4/2002 | Doherty et al. |
| 6,423,688 B1 | 7/2002 | Thorsett et al. |
| 6,645,939 B1 | 11/2003 | Durette et al. |
| 6,734,311 B2 | 5/2004 | Hagmann et al. |
| 6,900,179 B2 | 5/2005 | Thorsett et al. |
| 6,943,180 B2 | 9/2005 | Doherty et al. |
| 7,910,609 B2* | 3/2011 | DeGrado et al. ............. 514/327 |
| 8,258,159 B2* | 9/2012 | DeGrado et al. ............. 514/327 |
| 2003/0100585 A1 | 5/2003 | DuPlantier et al. |
| 2004/0072850 A1 | 4/2004 | Knegtel et al. |
| 2009/0197861 A1 | 8/2009 | DeGrado et al. |
| 2009/0233968 A1 | 9/2009 | DeGrado et al. |
| 2010/0179119 A1* | 7/2010 | DeGrado et al. .......... 514/210.17 |

FOREIGN PATENT DOCUMENTS

| | | | |
|---|---|---|---|
| WO | WO 03/008380 A1 | 1/2003 | |
| WO | WO 03/084984 | 10/2003 | |
| WO | WO 2006/133338 A1 | 12/2006 | |
| WO | WO 2006133388 | * 12/2006 | ............. A61K 38/00 |
| WO | WO 2007/027742 A2 | 3/2007 | |

OTHER PUBLICATIONS

Choi et al. Small Molecule Inhibitors of Integrin alpha2beta1. Journal of Medicinal Chemistry (2007), 50(22), 5457-5462.*
Vippagunta (S.R. Vippagunta, et al. Adv. Drug Delivery Rev. (2001) 48, pp. 3-26).*
Miller et al., Small-molecule inhibitors of integrin a2b1 that prevent pathological thrombus formation via an allosteric mechanism. Proceedings of the National Academy of Sciences of the United States of America (Jan. 20, 2009), 106(3), 719-724 (Applicant/Assignee Publication).*
U.S. Appl. No. 61/099,747, filed Sep. 24, 2008, DeGrado, et al.
U.S. Appl. No. 60/687,972, filed Jun. 7, 2005, DeGrado, et al.
U.S. Appl. No. 60/712,775, filed Aug. 31, 2005, Snyder et al.
Baronas-Lowell et al., "Differential Modulation of Human Melanoma Cell Metalloproteinase Expression by α2β1 Integrin and CD44 Triple-Helical Ligands Derived from Type IV Collagen", J. Biol. Chem., Oct. 15, 2004, 279(42), 43503-43513.
Bellavite et al., "A Colorimetric Method for the Measure of Platelet Adhesion in Microtiter Plates", Anal. Biochem., Feb. 1, 1994, 216(2), 444-450.
Bennett et al., "Agonist-Activated αvβ3 on Platelets and Lymphocytes Binds to the Matrix Protein Osteopontin", J. Biol. Chem., Mar. 28, 1997, 272(13), 8137-8140.

(Continued)

Primary Examiner — Maury Audet
(74) Attorney, Agent, or Firm — Baker & Hostetler, LLP

(57) ABSTRACT

Novel compounds inhibiting the integrin α2β1/GPIa-IIa receptor are disclosed. Also disclosed are pharmaceutical compositions containing the compounds, as well as methods of their therapeutic use. The compounds disclosed are useful, inter alia, as inhibitors of integrin α2β1/GPIa-IIa-mediated activity.

24 Claims, 4 Drawing Sheets

(56) References Cited

OTHER PUBLICATIONS

Bennett et al., "Exposure of platelet fibrinogen receptors by ADP and epinephrine", J. Clin. Invest., Nov. 1979, 64(5), 1393-1401.
Bennett, "Structure and function of the platelet integrin αIIbβ3", J. Clin. Invest., Dec. 2005, 115(12), 3363-3369.
Chen et al., "Reciprocal signaling by integrin and nonintegrin receptors during collagen activation of platelets", Mol Cell Biol., Jul. 2003, 23(14), 4764-4777.
Chen et al., "Evidence That Ligand and Metal Ion Binding to Integrin α4β1 are Regulated through a Coupled Equilibrium", J. Biol. Chem., Sep. 28, 2001, 276(39), 36520-36529.
Choi et al., "Small Molecule Inhibitors of Integrin α2β1", J. Med. Chem., Nov. 1, 2007, 50(22), 5457-5462.
Connors et al., "Two synergistic activation mechanisms of integrin α2β1 integrin-mediated collagen binding", J. Biol. Chem., May 11, 2007, 282(19), 14675-14683.
DeWood et al., "Prevalence of Total Coronary Occlusion During the Early Hours of Transmural Myocardial Infarction", N. Eng. J. Med., Oct. 16, 1980, 303(16), 897-902.
Emsley et al., "Crystal Structure of the I Domain from Integrin α2β1", J. Biol. Chem. Nov. 7, 1997, 272(45), 28512-28517.
Emsley et al., "Structural Basis of Collagen Recognition by Integrin α2β1", Cell, Mar. 31, 2000, 101(1), 47-56.
Ettmayer et al., "Lessons Learned from Marketed and Investigated Prodrugs", J. Med. Chem., May 6, 2004, 47(10), 2393-2404.
Falk et al., "Coronary Plaque Disruption", Circulation, Aug. 1, 1995, 92(3), 657-671.
Feire et al., "Cellular Integrins Function as Entry Receptors for Human Cytomegalovirus Via a Highly Conserved Disintegrin-Like Domain", Proc Natl Acad Sci USA, Oct. 26, 2004, 101(43), 15470-15475.
Ferarra, "The Role of Vascular Endothelial Growth Factor in Pathological Angiogenesis", Breast Cancer Res Treat., Jan. 1995, 36(2), 127-137.
Folkman, "Angiogenesis in Cancer, Vascular, Rheumatoid and Other Disease", Nat Med., Jan. 1, 1995, 1(1), 27-31.
Furihata et al., "Influence of platelet collagen receptor polymorphisms on risk for arterial thrombosis", Arch. Pathol. Lab. Med., Mar. 2002, 126(3), 305-309.
Fuster et al., "The Pathogenesis of Coronary Artery Disease and the Acute Coronary Syndromes (1)", N. Engl. J. Med., Jan. 23, 1992, 326(4), 242-250.
Graham et al., "Integrin-using rotaviruses bind α2β1 integrin α2 I domain via VP4 DGE sequence and recognize αXβ2 and αVβ3 by using VP7 during cell entry", J. Virol., Sep. 2003, 77(18), 9969-9978.
Hagmann, "The discovery and potential of N-sulfonylated dipeptide VLA-4 antagonists", Curr. Top Med. Chem., Oct. 2004, 4(14), 1461-1471.
Han et al., "Integrin α2β1 Recognizes Laminin-2 and Induces C-erb B2 Tyrosine Phosphorylation in Metastatic Human Melanoma Cells", Connect Tissue Res., Jan. 1999, 40(4), 283-293.
Han et al., "Targeted Prodrug Design to Optimize Drug Delivery", AAPS Pharmsci, Mar. 21, 2000, 2(1), Article 6, p. 1.
Handa et al., "Platelet unresponsiveness to collagen: involvement of glycoprotein Ia-IIa (α2β1 integrin) deficiency associated with a myeloproliferative disorder", Thromb. Haemost., Mar. 1995, 73, 521-528.
He et al., "The contributions of the α 2 β 1 integrin to vascular thrombosis in vivo. Blood", Nov. 15, 2003, 102(10), 3652-3657.
Holtkotter et al., "Integrin α2-deficient mice develop normally, are fertile, but display partially defective platelet interaction with collagen", J. Biol. Chem., Mar. 29, 2002, 277(13), 10789-10794.
Huryn et al., "Synthesis, characterization and evaluation of pro-drugs of VLA-4 antagonists", Bioorg. Med. Chem Lett., Apr. 5, 2004, 14(7), 1651-1654, Erratum in: Bioorg. Med. Chem. Lett., Nov. 1, 2004, 14(21), 5449.
Huryn et al., "The identification and optimization of orally efficacious, small molecule VLA-4 antagonists", Curr. Top. Med. Chem., Oct. 2004, 4(14), 1473-1484.
Hynes, "Integrins: bidirectional, allosteric signaling machines", Cell Review, Sep. 20, 2002, 110(6), 673-687.
Inoue et al., "Integrin α2β1 mediates outside-in regulation of platelet spreading on collagent through activation of Src Kinases and PLCgamma2", J. Cell Biol., Mar. 3, 2003, 160(5), 769-780.
Jackson et al., "Antiplatelet Therapy: In Search of the Magic Bullet", Nat. Rev. Drug. Discov., Oct. 2003, 2(10), 775-789.
Jung et al., "Platelets interact with soluble and insoluble collagens through characteristically different reactions", J Biol Chem., Jun. 12, 1998, 273(24), 14827-14837.
Jung et al., "Signal-transducing mechanisms involved in activation of the platelet collagen receptor integrin α2β1", J. Biol. Chem., Mar. 2000, 275, 8016-8026.
Kamenecka et al., "N-aryl-prolyl-dipeptides as potent antagonists of VLA-4", Bioorg. Med. Chem. Lett., Aug. 19, 2002, 12(16), 2205-2208.
Kehrel et al., "Deficiency of intact thrombospondin and membrane glycoprotein Ia in platelets with defective collagen-induced aggregation and spontaneous loss of disorder", Blood, Apr. 1988, 71(4), 1074-1078.
Knight et al., "The collagen-binding A-domains of integrins α(1)β(1) and α(2)β(1) recognize the same specific amino acid sequence, GFOGER, in native (triple-helical) collagens", J. Biol. Chem., Jan. 7, 2000, 275(1), 35-40.
Knutson et al., "CD44/Chondroitin Sulfate Proteoglycan and a 2 β 1 Integrin Mediate Human Melanoma Cell Migration on Type IV Collagen and Invasion of Basement Membranes", Mol. Biol. Cell., Mar. 1996, 7(3), 383-396.
Koo et al., "A small molecule very late antigen-4 antagonist can inhibit ovalbumin-induced lung inflammation", Am. J. Respir. Crit. Care Med., May 15, 2003, 167(10), 1400-1409.
Kritzik et al., "Nucleotide polymorphisms in the α2 gene define multiple alleles that are associated with differences in platelet α2 β1 density", Blood, Oct. 1, 1998, 92(7), 2382-2388.
Kufrin et al., "Antithrombotic thrombocytes: ectopic expression of urokinase-type plasminogen activator in platelets", Blood, Aug. 1, 2003, 102(3), 926-933.
Kuijpers et al., "Complementary roles of glycoprotein VI and α2β1 integrin in collagen-induced thrombus formation in flowing whole blood ex vivo", FASEB J., Apr. 2003, 17(6), 685-687.
Kumar, "Aseptic meningitis: Diagnosis and management", Indian J. Pediatr., Jan. 2005, 72(1), 57-63.
Kunicki et al., "Variability of integrin α2β1 activity on human platelets", Blood, Oct. 1993, 82, 2693-2703.
Leone et al., "An Assessment of the Mechanistic Differences Between Two Integrin α4β1 Inhibitors, the Monoclonal Antibody TA-2 and the Small Molecule BIO5192, in Rat Experimental Autoimmune Encephalomyelitis", The Journal of Pharmacology and Experimental Therapeutics, Jun. 1, 2003, 305(3), 1150-1162.
Lin et al., "Bioisosteric replacement of anilide with benzoxazole: potent and orally bioavailable antagonists of VLA-4", Bioorg. Med. Chem. Lett., May 3, 2004, 14(9), 2331-2334.
Londrigan et al., "Monkey rotavirus binding to α2β1 integrin requires the α2 I domain and is facilitated by the homologous β1 subunit", J. Virol., Sep. 2003, 77(17), 9486-501.
Lu et al., "Locking in Alternate Conformations of the Integrin αLβ2 I Domain with Disulfide Bonds Reveals Functional Relationships Among Integrin Domains", PNAS, Feb. 27, 2001, 98(5), 2393-2398.
Luo et al., "Structural basis of integrin signaling and regulation", Annu. Rev. Immunol. Aug. 2007, 25, 619-647.
Nieswandt et al., "Glycoprotein VI But Not α2β1 Integrin is Essential for Platelet Interaction With Collagen", EMBO J., May 1, 2001, 20(9), 2120-2130.
Nieswandt et al., "Platelet-Collagen Interaction: Is GPVI the Central Receptor?", Blood, Jul. 15, 2003, 102(2), 449-456.
Nieswandt et al., "Platelets in Atherothrombosis", Nat Med., Oct. 2002, 8(11), 1227-1234.
Nieuwenhuis et al., "Deficiency of Platelet Membrane Glycoprotein Ia Associated With a Decreased Platelet Adhesion to Subendothelium: A Defect in Platelet Spreading", Blood, Sep. 1986, 68(3), 692-695.

(56) References Cited

OTHER PUBLICATIONS

Nieuwenhuis et al., "Human blood platelets showing no response to collagen fail to express surface glycoprotein Ia", Nature, Dec. 5-11, 1985, 318(6045), 470-472.
Onley et al., "Micromolar Ca2+ concentrations are essential for Mg2+-dependent binding of collagen by the integrin α2β1 in human platelets", J. Biol. Chem., Aug. 11, 2000, 275(32), 24560-24564.
Pepinsky et al., "Comparative assessment of the ligand and metal ion binding properties of integrins α9β1 and α4β1", Biochemistry, Jun. 4, 2002, 41(22), 7125-7141.
Rosamond et al., "Heart disease and stroke statistics 2008 update. A report from the American Heart Association", Circulation Pre-published online: Dec. 17, 2007, 1-43.
Saelman et al., "Platelet Adhesion to Collagen Types I through VIII Under Conditions of Stasis and Flow is Mediated by GPIa/IIIa (α2β1-Integrin)", Blood, Mar. 1994, 83(5), 1244-1250.
Santoro, "Identification of a 160,000 Dalton Platelet Membrane Protein That Mediates the Initial Divalent Cation-dependent Adhesion of Platelets to Collagen", Cell, Sep. 12, 1986, 46(6), 913-920.
Santoro, "Platelet Surface Collagen Polymorphisms: Variable Receptor Expression and Thrombotic/Hemorrhagic Risk", Blood, Jun. 1, 1999, 93(11), 3575-3577.
Savage et al., "Influence of Fibrillar Collagen Structure on the Mechanisms of Platelet Thrombus Formation Under Flow", Blood, Oct. 15, 1999, 94(8), 2704-2715.
Senger et al., "The α(1)β(1) and α(2)β(1) Integrins Provide Critical Support for Vascular Endothelial Growth Factor Signaling, Endothelial Cell Migration, and Tumor Angiogenesis", Am. J. Pathol., Jan. 2002, 160(1), 195-204.
Senger et al., "Vascular Permeability Factor (VPF, VEGF) in Tumor Biology", Cancer Metastasis Rev., Sep. 1993, 12(3-4), 303-324.
Shattil et al., "Integrins: Dynamic Scaffolds for Adhesion and Signaling in Platelets", Blood, Sep. 15, 2004, 104(6), 1606-1615.
Shimaoka et al., "Small molecule integrin antagonists that bind to the β2 subunit I-like domain and activate signals in one direction and block them in the other", Immunity, Sep. 2002, 19(3), 391-402.
Siljander et al., "Platelet receptor interplay regulates collagen-induced thrombus formation in flowing human blood", Blood, Feb. 15, 2004, 103(4), 1333-1341.
Stasiak et al., "Sulphonamide-based small molecule VLA-4 antagonists", Bioorg. Med. Chem. Lett., Nov. 3, 2003, 13(21), 3875-3878.
Sweeney et al., "Angiogenesis in Collagen I Requires α2β1 Ligation of a GFP*GER Sequence and Possibly p38 MAPK Activation and Focal Adhesion Disassembly", J. Biol. Chem., Aug. 15, 2003, 278(33), 305,16-24.
Takagi et al., "Global conformational rearrangements in integrin extracellular domains in outside-in and inside-out signaling", Cell, Sep. 6, 2002, 110(5), 599-611.
Tam et al., "Abciximab (ReoPro, chimeric 7E3 Fab) demonstrates equivalent affinity and functional blockade of glycoprotein IIb/IIIa and αvβ3 integrins", Circulation, Sep. 15, 1998, 98, 1085-1091.
Testa, "Prodrug Research: Futile or Fertile?", Biochem. Pharmacol., Jul. 2004, 68, 2097-2106.
Triantafilou et al., "A biochemical approach reveals cell-surface molecules utilised by Picornaviridae: Human Parechovirus 1 and Echovirus 1", J. Cell Biochem., Mar. 2001, 80(3), 373-381.
Tuckwell et al., "Integrin α2 I-domain is a binding site for collagens", J. Cell Sci., Apr. 1995, 108(Pt 4), 1629-1637.
Vippagunta et al., "Crystalline Solids", Advanced Drug Delivery Reviews, Dec. 2001, 48, 3-26.
Watson et al., "Collagen receptor signaling in platelets: extending the role of the ITAM", Immunol. Today, Jun. 1998, 19, 260-264.
Welzenbach et al., "Small molecule inhibitors induce conformational changes in the Idomain and the I-like domain of lymphocyte function-associated antigen-1", J. Biol. Chem., Mar. 22, 2002, 277, 10590-10598.
White et al., "The Leech Product Saratin is a Potent Inhibitor of Platelet Integrin α2β1 and von Willebrand Factor Binding to Collagen", FEBS J., Mar. 2007, 274(6), 1481-1491.
Yang et al., "Integrin α1β1 and α2β1 are the Key Regulators of Hepatocarcinoma Cell Invasion Across the Fibrotic Matrix Microenvironment", Cancer Res., Dec. 1, 2003, 63(23), 8312-8317.
Patani et al., "Bioisosterism: A Rational Approach in Drug Design," Chem. Rev. Dec. 19, 1996, 96(8), 3147-3176.

* cited by examiner

INHIBITORS OF INTEGRIN ALPHA2BETA1 BASED ON PROLYL DIAMINOPROPIONIC ACID SCAFFOLD

CROSS REFERENCE TO RELATED APPLICATIONS

The present application claims priority to U.S. Provisional App. No. 61/099,747, filed Sep. 24, 2008, the contents of which are hereby incorporated by reference in their entirety. This application is also a continuation-in-part of U.S. Ser. No. 12/237,015, filed Sep. 24, 2008, which is a continuation of U.S. Ser. No. 11/916,746, filed Dec. 8, 2008 which is a U.S. National Stage Entry of PCT/US06/22225 filed Jun. 7, 2006, which claims priority from U.S. Provisional App. No. 60/687,972, filed Jun. 7, 2005. Each of these applications are hereby incorporated by reference in their entirety. This application is also a continuation-in-part of U.S. Ser. No. 11/916,746, which was filed Dec. 9, 2008.

GOVERNMENT RIGHTS

The United States Government may have rights in the invention described herein, which was made in part with funding from the National Center for Research Resources (U.S. National Institutes of Health), Grant No. UL1RR024134.

TECHNICAL FIELD

The present invention relates to "small" molecule inhibitors of the α2β1/GPIa-IIa integrin, as well as methods of production, use, and therapeutic administration thereof.

BACKGROUND

Recruitment, adhesion, and aggregation of platelets at sites of vascular injury are critical to generation of beneficial blood clotting events. However, excessive accumulation of platelets, e.g., at sites of ruptured atherosclerotic plaques, can give rise to the development of acute coronary syndromes, stroke, ischaemic complications of peripheral vascular disease, and other disease states. Fuster, V., Badimon, L., Badimon, J. J. & Chesebro, J. H. *The Pathogenesis of Coronary Artery Disease and the Acute Coronary Syndromes* (1). *N. Engl. J. Med.* 326, 242-250 (1992); Falk, E, Shah, P. K. & Fuster, V. *Coronary Plaque Disruption. Circulation* 92, 657-671 (1995). Promise for enhanced clinical management of such vascular diseases has arisen in recent years with progress in understanding of the mechanisms underlying the formation of arterial plaque and thrombosis and of the criticality of the role of platelet activity in the development of cardiovascular disease.

Tempered by the understanding that antithrombotic treatment should be effective and yet avoid undermining hemostasis, clinicians of cardiovascular disease prevention and treatment have depended on mild therapeutic agents like aspirin and clopidogrel for widespread application. There are a variety of other antithrombotic drugs, including coumadin and abciximab (ReoPro®), ticlopidine, and others, but there remains an urgent need for newer and safer antithrombotics, to address stroke, deep vein thrombosis (DVT), myocardial infarction, coronary artery disease, cerebrovascular disease, peripheral arterial disease, diabetes mellitus, atrial fibrillation, congestive heart failure, and other vascular disorders. Jackson S P and Schoenwaelder S M *Antiplatelet Therapy: In Search of the 'Magic Bullet'. Nat. Rev. Drug. Discov.* 2(10), 775-89 (2003). *Review.* More versatile and effective and yet selective and safe therapeutic agents are currently the object of extensive research worldwide, especially in light of the increasing prevalence of cardiovascular disease both due to changes in diet and lifestyle and in view of the aging of the population. Special emphasis has been placed on the issue of improving efficacy without compromising safety, since all forms of presently available antithrombotic therapies cannot be administered at potent doses without producing negative physiological conditions, primarily bleeding events.

Upon vessel injury and attendant removal or damage of the protective endothelial lining, platelets encounter a diverse set of proteins from the connective tissue of the vessel wall. These include collagen and von Willebrand factor (vWf). Platelet adhesion to these proteins and subsequent activation is mediated by a multitude of platelet receptors. Adhesion of platelets to the extracellular matrix triggers a series of signaling events that ultimately result in formation of a hemostatic plug known as a thrombus. Recent findings provide strong evidence that immediately following vessel rupture, the platelet receptor GPVI binds loosely to exposed collagen, which is alone insufficient to induce stable platelet adhesion, but which triggers a tyrosine kinase-based signaling pathway that results in major conformational changes and attendant activation in specific receptors, including integrin α2β1. Emsley J, Knight C G, Farndale R W, Barnes M J, Liddington R C. *Structural Basis of Collagen Recognition by Integrin Alpha2Beta1. Cell.* 101(1), 47-56 (2000).

Integrin α2β1, also known as platelet GPIa-IIa, was the first collagen receptor to be identified on platelets. Nieuwenhuis H K, Akkerman J W, Houdijk W P, Sixma J J. *Human Blood Platelets Showing No Response to Collagen Fail to Express Surface Glycoprotein Ia. Nature.* 318(6045), 470-2 (1985); Santoro S A. *Identification of a 160,000 Dalton Platelet Membrane Protein That Mediates the Initial Divalent Cation-dependent Adhesion of Platelets to Collagen. Cell.* 46(6), 913-20 (1986). Similar to other members of the integrin family, α2β1 links the cytoskeleton of the cell with the extracellular matrix. Hynes R O. *Integrins: bidirectional, allosteric signaling machines. Cell.* 110(6):673-87. Review (2002). Besides playing an essential role in adhesion to the extracellular matrix, integrins are indispensable for cellular signaling. All integrins are heterodimers, consisting of an α subunit and a β subunit. About half of the known mammalian integrins, including α2β1, have an I-domain inserted into the α subunit (Hynes, 2002). In these cases, the I-domain is responsible for binding of the integrin to its natural ligand(s). A specific amino acid sequence in collagen, GFOGER (O=hydroxyproline), promotes stable binding to the I-domain of α2β1. Onley D J, Knight C G, Tuckwell D S, Barnes M J, Farndale R W. *Micromolar Ca2+ concentrations are essential for Mg2+-dependent binding of collagen by the integrin alpha 2beta 1 in human platelets. J Biol. Chem.* 275(32):24560-4 (2000). Binding occurs in a cation dependent manner, supported by either magnesium or manganese Tuckwell D, Calderwood D A, Green L J, Humphries M J. *Integrin alpha 2 I-domain is a binding site for collagens. J Cell Sci.* 108(Pt 4):1629-37 (1995). A crystal structure of a complex between the I-domain of α2β1 and a triple helical peptide containing the GFOGER sequence has been solved. Emsley J, Knight C G, Farndale R W, Barnes M J, Liddington R C. *Structural basis of collagen recognition by integrin alpha2beta1. Cell.* 101(1), 47-56 (2000). A glutamic acid (E) from the middle strand of the triple helix coordinates to metal-ion dependent adhesion site (MIDAS) while other residues of the GFOGER motif from the middle and trailing strands interact with complementary sites on the I-domain surface.

Importantly, integrin α2β1 has multiple states of activation which can be regulated from inside or outside of the cell. Hynes R O. *Integrins: bidirectional, allosteric signaling machines. Cell.* 110(6):673-87. Review (2002). For instance, signaling through the platelet receptor GPVI impinges upon the cytoplasmic domain of α2β1, which results in a dramatic conformational change that eventually propagates along the α2β1 integrin, ultimately affecting the I-domain at the integrin's head. Integrin activation is induced by several other platelet agonists, including ADP and thrombin. Jung S M, Moroi M. *Platelets interact with soluble and insoluble collagens through characteristically different reactions. J Biol. Chem.* 273(24):14827-37 (1998). The activated integrin can than bind tightly to collagen. This adhesion can potentially be blocked with either a direct competitor of the collagen/I-domain interaction or with an allosteric regulator, the latter of which precludes activation of the I domain. Two types of small-molecule inhibitors have been developed for a related integrin, αLβ2. Shimaoka M, Salas A, Yang W, Weitz-Schmidt G, Springer T A. *Small molecule integrin antagonists that bind to the beta2 subunit I-like domain and activate signals in one direction and block them in the other. Immunity.* 19(3):391-402 (2002). The first binds to the I-domain of αLβ2 at a distant site from the MIDAS, blocking activation of its I domain and subsequent binding to ICAM-1. The second binds to the I-like domain of the β subunit, which is located directly beneath the I domain. A direct competitive inhibitor of an I-domain/ligand interaction has not yet been reported.

Despite the fact that α2β1 integrin was discovered more than 15 years ago, its precise role in platelet adhesion and aggregation remains controversial. This is partially due to the overlapping functions of α2β1 and GPVI. Chen H, Kahn M L. *Reciprocal signaling by integrin and nonintegrin receptors during collagen activation of platelets. Mol Cell Biol.* 23(14): 4764-77 (2003). Integrin α2β1 is essential for platelet adhesion and activation on monomeric type I collagen; it has been demonstrated through platelet analysis that adhesion and thrombus growth on pepsin-solubilized type I collagen under low and high shear flow conditions is absolutely dependent on functional α2β1. Savage B, Ginsberg M H, Ruggeri Z M. *Influence of Fibrillar Collagen Structure on the Mechanisms of Platelet Thrombus Formation Under Flow. Blood.* 94(8), 2704-15 (1999); Nieswandt B, Brakebusch C, Bergmeier W, Schulte V, Bouvard D, Mokhtari-Nejad R, Lindhout T, Heemskerk J W, Zirngibl H, Fassler R. *Glycoprotein VI But Not Alpha2Beta1 Integrin is Essential For Platelet Interaction With Collagen. EMBO J.* 20(9), 2120-30 (2001). However, on the more physiologically relevant insoluble collagen (fibrillar collagen), α2β1 integrin may be dispensable, at least in the context of hemostasis. Nieswandt B, Watson S P. *Platelet-Collagen Interaction: Is GPVI the Central Receptor? Blood.* 102(2), 449-6 (2003). Review. For instance, fibrillar collagen-induced aggregation of β1-null mouse platelets is not reduced, despite a slight time delay. Nieswandt B, Brakebusch C, Bergmeier W, Schulte V, Bouvard D, Mokhtari-Nejad R, Lindhout T, Heemskerk J W, Zirngibl H, Fassler R. *Glycoprotein VI But Not Alpha2Beta1 Integrin is Essential For Platelet Interaction With Collagen. EMBO J.* 20(9), 2120-30 (2001). Furthermore, the β1-null platelets adhere normally to fibrillar collagen under static conditions. Nonetheless, it has been established that adhesion under physiological conditions of blood flow requires a functional α2β1 integrin. Siljander P R, Munnix I C, Smethurst P A, Deckmyn H, Lindhout T, Ouwehand W H, Farndale R W, Heemskerk J W. *Platelet receptor interplay regulates collagen-induced thrombus formation in flowing human blood. Blood.* 103(4): 1333-41 (2004).

Studies of platelets derived from two individuals with an integrin α2β1 deficiency have demonstrated a defect in adhesion and spreading on the subendothelium. Nieswandt B, et al. (2001); Ruggeri Z M. *Platelets In Atherothrombosis. Nat. Med.* 8(11), 1227-34 (2002). Review. Indeed, these patients exhibit only modest degree of defect in hemostasis, manifested as only minor bleeding complications. Nieuwenhuis H K, et al., *Nature.* 318(6045), 470-2 (1985); Nieuwenhuis H K, Sakariassen K S, Houdijk W P, Nievelstein P F, Sixma J J. *Deficiency of Platelet Membrane Glycoprotein Ia Associated With a Decreased Platelet Adhesion to Subendothelium: A Defect in Platelet Spreading. Blood.* 68(3), 692-5 (1986). This has important implications for the search for antithrombotic therapies with favorable safety profiles. It suggests that antagonism of α2β1 integrin will have a beneficially mild antithrombotic effect; increasing amount of evidence indeed suggests that α2β1 may have a greater role in pathological thrombosis relative to normal hemostasis. This observation may reflect the fact that an increased amount of collagen accumulates in diseased blood vessels. For instance, the extracellular matrix around an atheroslerotic lesion is heavily enriched in collagens. Nieswandt B, et al., (2003). Besides providing an adhesive support for platelets, collagen sends potent prothrombotic signals into the cell through interaction with its platelet receptors. Overexpression of α2β1 integrin has been linked to cardiovascular disease in humans. Kritzik M, Savage B, Nugent D J, Santoso S, Ruggeri Z M, Kunicki T J. *Nucleotide polymorphisms in the alpha2 gene define multiple alleles that are associated with differences in platelet alpha2 beta1 density. Blood.* 92(7):2382-8 (1998). Furthermore, recent in vivo data indicates that α2β1-deficient mice have delayed thrombus formation following carotid artery injury. He L, Pappan L K, Grenache D G, Li Z, Tollefsen D M, Santoro S A, Zutter M M. *The contributions of the alpha 2 beta 1 integrin to vascular thrombosis in vivo. Blood.* 102 (10):3652-7 (2003). These data reveal a critical role for α2β1 in thrombosis. Hence, the α2β1 integrin is an important pharmacological target for cardiovascular diseases, and the resulting treatment is expected to be well-tolerated and provide long-term antithrombotic protection.

Equally significant, the α2β1 integrin may be a target for cancer, several types of viral infections, and other pathologies. Overexpression of α2β1 in various types of cancer cells, particularly in human melanoma cells and hepatocellular carcinomas, has been linked to tumor metastasis. Han J, Jenq W, Kefalides N A. *Integrin Alpha2Beta1 Recognizes Laminin-2 and Induces C-erb B2 Tyrosine Phosphorylation in Metastatic Human Melanoma Cells. Connect Tissue Res.* 40(4), 283-93 (1999). Yang C, Zeisberg M, Lively J C, Nyberg P, Afdhal N, Kalluri R. *Integrin Alpha1Beta1 and Alpha2Beta1 Are the Key Regulators of Hepatocarcinoma Cell Invasion Across the Fibrotic Matrix Microenvironment. Cancer Res.* 63(23), 8312-7 (2003). The α2β1 integrin is known to be the primary melanoma cell adhesion molecule for type IV collagen, indicating a key role for that integrin in pathological metastasis Knutson J R, Lida J, Fields G B, McCarthy J B. *CD44/Chondroitin Sulfate Proteoglycan and Alpha 2 Beta 1 Integrin Mediate Human Melanoma Cell Migration on Type IV Collagen and Invasion of Basement Membranes. Mol Biol Cell.* 7(3), 383-96 (1996). Ligand binding by the α2β1 integrin triggers a series of intracellular signaling events that ultimately result in the release of cytokines and proteases, both of which are beneficial for tumor cell progression. Baronas-Lowell D, Lauer-Fields J L, Borgia J A, Sferrazza G F, Al-Ghoul M, Minond D, Fields G B. *Differential Modulation of Human Melanoma Cell Metalloproteinase Expression by Alpha2Beta1 Integrin and CD44 Triple-Helical Ligands*

Derived from Type IV Collagen. *J Biol. Chem.* 279(42), 43503-13 (2004). Furthermore, antagonism of the α2β1 integrin suppresses angiogenesis. Senger D R, Perruzzi C A, Streit M, Koteliansky V E, de Fougerolles A R, Detmar M. *The Alpha(1)Beta(1) and Alpha(2)Beta(1) Integrins Provide Critical Support For Vascular Endothelial Growth Factor Signaling, Endothelial Cell Migration, and Tumor Angiogenesis. Am J Pathol.* 160(1), 195-204 (2002). This has profound implications since angiogenesis is involved in growth and metastasis of solid tumors, rheumatoid arthritis, diabetic retinopathy, and a variety of other important disease states. Folkman J. *Angiogenesis in Cancer, Vascular, Rheumatoid and Other Disease. Nat. Med.* 1(1), 27-31 (1995). *Review*; Senger D R, Van de Water L, Brown L F, Nagy J A, Yeo K T, Yeo T K, Berse B, Jackman R W, Dvorak A M, Dvorak H F. *Vascular Permeability Factor (VPF, VEGF) in Tumor Biology. Cancer Metastasis Rev.* 12(3-4), 303-24 (1993). *Review*; Ferarra, N. *The Role of Vascular Endothelial Growth Factor in Pathological Angiogenesis. Breast Cancer Res Treat.* 36(2), 127-37 (1995). *Review*. Specific blocking of α2β1 function halts capillary morphogenesis, the essential antecedent to angiogenesis, whereas blocking of related integrin dimers or monomer subunits does not similarly arrest morphogenesis. Sweeney S M, DiLullo G, Slater S J, Martinez J, Iozzo R V, Lauer-Fields J L, Fields G B, San Antonio J D. *Angiogenesis in Collagen I Requires Alpha2Beta1 Ligation of a GFP\*GER Sequence and Possibly p38 MAPK Activation and Focal Adhesion Disassembly. J Biol. Chem.* 278(33), 30516-24 (2003). Antagonism of the α2β1 integrin also curbs haptotactic endothelial cell migration, Senger D R et al., a critical step in extravasation of tumor cells into secondary tissues.

It has also recently been shown that human cytomegalovirus (HCMV), which is extremely promiscuous and responsible for significant mortality, requires the presence of α2β1 to penetrate a cell. Feire A L, Koss H, Compton T. *Cellular Integrins Function as Entry Receptors For Human Cytomegalovirus Via a Highly Conserved Disintegrin-Like Domain. Proc Natl Acad Sci USA.* 101(43), 15470-5 (2004). Likewise, integrin α2β1 has been strongly implicated in rotavirus cell attachment and entry. Graham K L, Halasz P, Tan Y, Hewish M J, Takada Y, Mackow E R, Robinson M K, Coulson B S. *Integrin-using rotaviruses bind alpha2beta1 integrin alpha2 I domain via VP4 DGE sequence and recognize alphaXbeta2 and alphaVbeta3 by using VP7 during cell entry. J. Virol.* 77(18), 9969-78. (2003). Rotaviruses are leading causes of acute gastroenteritis in human infants and young children and animals around the globe. Id. It has been demonstrated that inhibition of the α2β1 integrin forestalls cell binding and infection by rotaviruses. Londrigan S L, Graham K L, Takada Y, Halasz P, Coulson B S. *Monkey rotavirus binding to alpha2beta1 integrin requires the alpha2 I domain and is facilitated by the homologous beta1 subunit. J. Virol.* 77(17), 9486-501 (2003). Similarly, viruses of the Piconaviridae family, such as Echovirus 1 (Echo1), have also been shown to utilize the α2β1 integrin during the cell-infection cycle. Triantafilou K & Triantafilou M. *A biochemical approach reveals cell-surface molecules utilised by Picornaviridae: Human Parechovirus 1 and Echovirus 1. J Cell Biochem.* 80(3), 373-81 (2001). Echo viruses are implicated in numerous human pathologies; for example, certain forms of aseptic meningitis and acute respiratory illness are known to be caused by the Echo-1 virus. See, e.g., Kumar R. *Aseptic meningitis: Diagnosis and management. Indian J Pediatr.* 72(1), 57-63 (2005).

Inhibition of the α2β1 integrin may prove effective in impeding binding and entry of these problematic and medically-significant viruses, and in treatment of cancers and other disease states concerning which α2β1 expression and functionality is a significant factor, and previous efforts have been made to provide compounds possessing α2β1 integrin inhibitory activity. See Takayanagi, M et al., WO 03/008380. As yet, however, there is an unfulfilled need in these respects.

SUMMARY

The present invention provides inhibitors of integrin α2β1 and methods for their synthesis and use.

In one aspect, provided are compounds having the formula I:

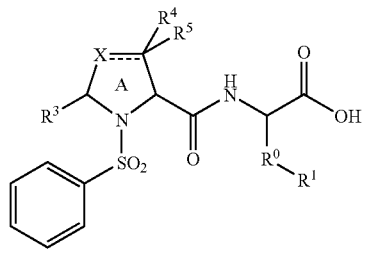

wherein:
X is alkylene, N, O, S, or $SO_2$;
$R^0$ is alkylene;
$R^1$ is —NHC(=O)$R^2$;
$R^2$ is —NH(CH$_2$)aryl;
$R^3$ is H, alkyl, aryl, or aralkyl, or forms a three- to six-membered carbocyclic or heterocyclic ring together with X and the carbon atom to which $R^3$ and X are both attached;
$R^4$ and $R^5$ are each independently H or —CH$_3$;
wherein
 the dashed line may represent a double bond;
 if $R^4$ and $R^5$ are both H, then
  X is $SO_2$; or,
  X is S and $R^3$ is not H; or,
  X is —CH— and the dashed line represents a double bond;
 and,
 if X is ethylidene, then one carbon atom of X, $R^3$, and the carbon atom to which both are attached form a three- to six-membered carbocyclic or heterocyclic ring, or,
  X forms a fused bicycle together with Ring A;
or a stereoisomer, partial stereoisomer, prodrug, pharmaceutically acceptable salt, hydrate, solvate, acid hydrate, or N-oxide thereof.

In another aspects, the present invention is directed to methods for treating at least one α2β1-affected disease state or infection comprising administering to a subject in need thereof a composition comprising a therapeutically effective amount of a compound having the formula I.

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

The present invention is directed to, among other things, "small" molecule inhibitors of the α2β1 integrin, as well as to methods of their use for treatment of the range of α2β1-affected disease states. These include, vascular conditions, diabetes- or rheumatoid arthritis-related conditions, cancers, viral infections, and other conditions or infections. The present invention represents a versatile and effective, yet selective and safe therapeutic regime for the treatment of α2α1-affected disease states, conditions, and infections.

Figure 1:
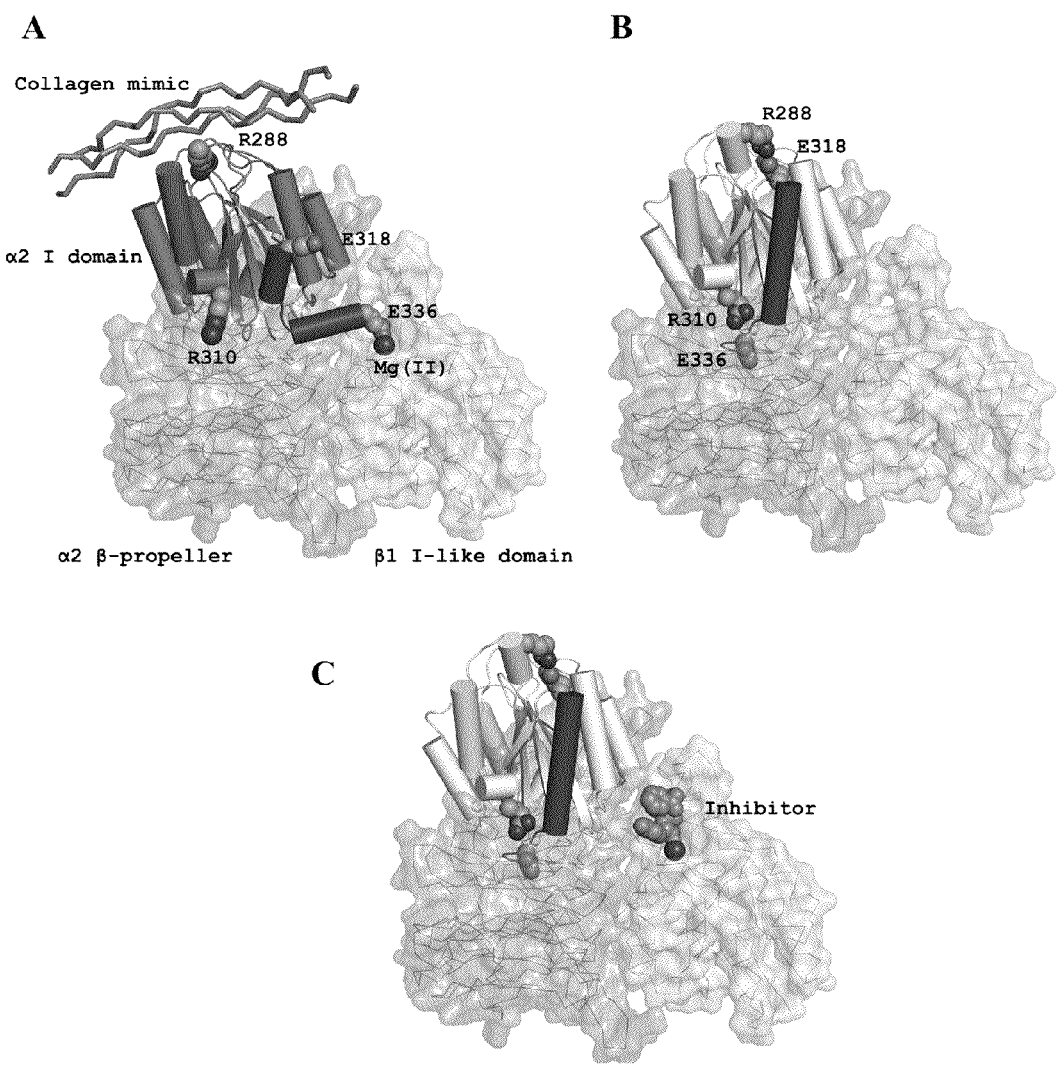
FIG. 1 depicts (A) the active conformation of integrin $α_2β_1$ bound to collagen with the C-terminal α7 helix of the I-domain displaced downwards to engage the metal ion in the I-like domain; (B) the inactive conformation of integrin $α_2β_1$ with stabilizing salt bridges formed by the pair E318 and 8288 as well as R310 and E338; and, (C) an inhibitor docked into integrin $α_2β_1$ I-like domain locking the compound into the inactive conformation

Integrins are α/β heterodimers whose conformational states are regulated by intracellular signaling pathways.[8, 9] I-domain-containing integrins differ from other integrins by virtue of having an inserted domain (I-domain) in their α subunit that is responsible for binding extracellular ligands. No crystallographic or NMR structures have been solved for intact I-domain containing integrins, although crystal structures for the isolated I-domains are available.[10] The mechanism of activation of the ligand-binding I-domain has been inferred through comparison with better known non-I-domain integrins such as $\alpha_{IIb}\beta_3$ and $\alpha_v\beta_3$ for which more high-resolution structural information is available. The I-domain is homologous to the ligand binding domain of integrins $\alpha_{IIb}\beta_3$ and $\alpha_4\beta_1$, and it directly binds ligand in its "open" conformation exposing a high-affinity active site. [11,12] The β subunit I-like domain regulates the switch of the I-domain from a "closed," inactive conformation to an "open," active conformation:[13, 14] Thus, the affinity of the I-domain for its ligand is regulated by downward displacement of its C-terminal α7 helix into the β subunit I-like domain (FIG. 1).[15] A class of LFA-1 (integrin $\alpha_L\beta_2$) antagonists previously believed to be I-domain inhibitors were proposed to function by a novel allosteric inhibitory mechanism: by binding the I-like domain, the inhibitors lock the integrin into its inactive conformation.[16]

A variety of small molecules have been found that weakly inhibit activation of integrin $\alpha_2\beta_1$ including naturally occurring collagen-mimetic peptides that bind the I-domain[17-19] and lipophilic compounds that stabilize a hydrophobic patch in the I-domain exposed in the inactive conformation:[20]

Herein are disclosed high affinity small molecule inhibitors of integrin $\alpha_2\beta_1$ related to the LFA-1 inhibitors that inhibit the I-like domain.

In the absence of an x-ray crystal structure for full length α2β1, utilization of computational methods and structure-activity relationships (SAR) are important for the development of active inhibitors and for understanding integrin biology. The present invention has resulted in part from the investigation of pharmacological activity of proline derivatives of the prolyl-2,3-diaminopropionic acid scaffold:

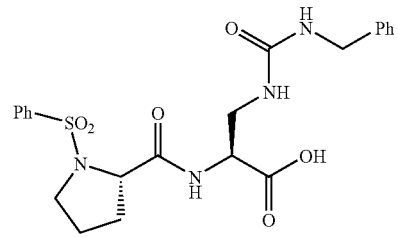 [SMILES: O=C(NCc1ccccc1)NC[C@H](NC(=O)[C@@H]1CCCN1S(=O)(=O)c1ccccc1)C(=O)O]

As described more fully infra, inhibitor tolerance for different ring sizes, other heterocycles, and further substitutions were investigated. In addition, molecular modeling was used to probe proline ring geometry and conformation. Homology modeling was applied based on the crystal structure of tirofiban bound to the I-like domain of αIIbβ3 to determine the conformation of inhibitors in the binding site and to investigate the selectivity of the compounds for α2β1. Such approaches and others resulted in the discovery of highly potent and selective α2β1 inhibitors that demonstrate in vivo efficacy in numerous respects.

The disclosures of each patent, patent application, and publication cited or described in this document are hereby incorporated herein by reference, in their entirety. Unless otherwise provided, superscript numbers appearing in brackets (i.e., "[x]") refer to the correspondingly-numbered publication listed in the final paragraph of the present application preceding the claims, each of which publications are hereby incorporated herein by reference in their entirety.

As employed above and throughout the disclosure, the following terms and abbreviations, unless otherwise indicated, shall be understood to have the following meanings "DAP" or "Dap" denotes 2,3-diaminopropionic acid.

"EDC" stands for 1-(3-Dimethylaminopropyl)-3-ethylcarbodiimide hydrochloride.

"HOBT" means 1-Hydroxybenzotriazole hydrate.

Protective groups are abbreviated according to the system disclosed in Greene, T. W. and Wuts, P. G. M., *Protective Groups in Organic Synthesis* 2d. Ed., Wiley & Sons, 1991, which is incorporated in its entirety herein. For example, "CBZ" or "Cbz" or "Z" stands for carbobenzyloxy or benzyloxycarbonyl, "Boc" or "BOC" represents t-butoxycarbonyl, "Alloc"/"Aloc" denotes allyloxycarbonyl, "Bz" means benzoyl, and "Fmoc" stands for 9-fluorenylmethoxycarbonyl.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compound and equivalents thereof known to those skilled in the art, and so forth. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" refers to a value of 7.2 to 8.8, inclusive; as another example, the phrase "about 8%" refers to a value of 7.2% to 8.8%, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", and the like.

As used herein, the terms "component," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

The abbreviations in the specification correspond to units of measure, techniques, properties, or compounds as follows: "min" means minute(s), "g" means gram(s), "mg" means milligram(s), "µg" means microgram(s), "eq" means equivalent(s), "h" means hour(s), "µL" means microliter(s), "mL" means milliliter(s), "mM" means millimolar, "M" means molar, "mmol" or "mmole" means millimole(s), "cm" means centimeters, "SEM" means standard error of the mean, and "IU" means International Units. "$IC_{50}$ value" or "$IC_{50}$" means dose of the compound which results in 50% alleviation or inhibition of the observed condition or effect.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein).

"Amino" refers to —$NH_2$ and may include one or more substituents that replace hydrogen.

As used herein, "aryl", "arene", and "aromatic" each refer to an optionally substituted, mono-, di-, tri-, or other multicyclic aromatic ring system having from about 5 to about 50 carbon atom ring members (and all combinations and subcombinations of ranges and specific numbers of carbon atoms therein), with from about 6 to about 10 carbon ring atom members being preferred.

As used herein, "alkenyl" refers to an alkyl radical having from about 2 to about 20 carbon atoms and one or more double bonds (and all combinations and subcombinations of ranges and specific numbers of carbon atoms therein), wherein alkyl is as previously defined. In some embodiments, it is preferred that the alkenyl groups have from about 2 to about 6 carbon atoms. Alkenyl groups may be optionally substituted.

"Alkylidene" signifies

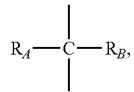

in which $R_A$ and $R_B$ are independently H or a substituent (exemplary "substituents" being described infra). For example, "ethylidene" refers to a bivalent radical represented by —($CR_CR_D$—$CR_ER_F$)—, wherein $R_C$, $R_D$, $R_E$, and $R_F$ are independently H or any suitable substituent.

As used herein, "aralkyl" refers to alkyl radicals bearing one or more aryl substituents and having from about 6 to about 50 carbon atoms (and all combinations and subcombinations of ranges and specific numbers of carbon atoms therein), wherein aryl and alkyl are as previously defined. In some preferred embodiments, the alkyl moieties of the aralkyl groups have from about 1 to about 4 carbon atoms. In other preferred embodiments, the alkyl moieties have from about 1 to about 3 carbon atoms. Aralkyl groups may be optionally substituted.

"Alkylamino" signifies alkyl-(NH)—, wherein alkyl is as previously described and NH is defined in accordance with the provided definition of amino. "Arylamino" represents aryl-(NH)—, wherein aryl is as defined herein and NH is defined in accordance with the provided definition of amino. Likewise, "aralkylamino" is used to denote aralkyl-(NH)—, wherein aralkyl is as previously defined and NH is defined in accordance with the provided definition of amino. "Alkoxy" as used herein refers to the group R—O— where R is an alkyl group, and alkyl is as previously described. "Aralkoxy" stands for R—O—, wherein R is an aralkyl group as previously defined. "Alkylsulfonyl" means alkyl-$SO_2$—, wherein alkyl is as previously defined.

As used herein, "alkylene" refers to an optionally branched or substituted bivalent alkyl radical having the general formula —$(CH_2)_n$—, where n is 1 to 10. Non-limiting examples include methylene, trimethylene, pentamethylene, and hexamethylene.

As used herein, "heteroaryl" refers to an aryl radical wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members are preferred. Likewise, a "heterocyclic ring" may be an aryl radical wherein one or more of the carbon atom ring members is independently replaced by a heteroatom group selected from the group consisting of S, O, N, and NH. Heterocyclic rings having a total from about 5 to 14 carbon atom ring members and heteroatom ring members are preferred.

"Halo" and "halogen" each refers to a fluoro, chloro, bromo, or iodo moiety, with fluoro, chloro, or bromo being preferred.

The phrase reading "D is optional" means that the substituents to which D is attached may be directly attached to each other. For example, in some preferred embodiments, A is attached directly to E by a bond.

Typically, substituted chemical moieties include one or more "substituents" that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—$NO_2$), cyano (—CN), amino (—$NH_2$), —N-substituted amino (—NHR"), —N,N-disubstituted amino (—N(R")R"), oxo (═O), carboxy (—COOH), —O—C(═O)R", —C(═O)R", —OR", —C(═O)OR", -(alkylene)-C(═O)—OR", —NHC(═O)R", aminocarbonyl (—C(═O)$NH_2$), —N-substituted aminocarbonyl (—C(═O)NHR"), —N,N-disubstituted aminocarbonyl (—C(═O)N(R")R"), thiol, thiolato (—SR"), sulfonic acid (—$SO_3H$), phosphonic acid (—$PO_3H$), —P(═O)(OR")OR", —S(═O)R", —S(═O)$_2$R", —S(═O)$_2$ $NH_2$, —S(═O)$_2$NHR", —S(═O)$_2$NR"R", —NHS(═O)$_2$R", —NR"S(═O)$_2$R", —$CF_3$, —$CF_2CF_3$, —NHC(═O)NHR", —NHC(═O)NR"R", —NR"C(═O) NHR", —NR"C(═O)NR"R", —NR"C(═O)R" and the like. In relation to the aforementioned substituents, each moiety R" can be, independently, any of H, alkyl, cycloalkyl, alkenyl, aryl, aralkyl, heteroaryl, or heterocycloalkyl, for example.

As used herein, the terms "treatment" or "therapy" (as well as different word forms thereof) includes preventative (e.g., prophylactic), curative or palliative treatment.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects. As an example, the compounds useful in the methods of the present invention are administered at a dosage and for a time such that the level of activation and adhesion activity of platelets is reduced as compared to the level of activity before the start of treatment.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

"Hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer >1) including, for example, dihydrates ($R.2H_2O$), trihydrates ($R.3H_2O$), and the like, or hemihydrates, such as, for example, $R.n_{/2}H_2O$, $R.n_{/3}H_2O$, $R.n_{/4}H_2O$ and the like wherein n is an integer.

"Solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer >1) including, for example, disolvates (R.2(solvent)), trisolvates (R.3(solvent)), and the like, or hemisolvates, such as, for example, $R.n_{/2}$(solvent), $R.n_{/3}$(solvent), $R.n_{/4}$(solvent) and the like wherein n is an integer. Solvents herein include mixed solvents, for example, methanol/water, and as such, the solvates may incorporate one or more solvents within the solvate.

"Acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

The term "stereoisomers" refers to compounds that have identical chemical constitution, but differ as regards the arrangement of the atoms or groups in space.

"Racemic" means having the capacity for resolution into forms of opposed optical activity.

As used herein, the term "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

"Prodrug" refers to compounds which are themselves inactive or minimally active for the activity desired, but through biotransformation can be converted into biologically active metabolites. For example, a prodrug of the present invention would include, inter alia, any compound which is convertible in vivo by metabolic means to a compound claimed or described in the present disclosure.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

As used herein, the terms "modulation" or "mediation" refer to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

In the present disclosure, the term "inhibitor" is intended to comprise any compound or agent, e.g., antibody, small molecule, peptide, oligopeptide, polypeptide, or protein, preferably small molecule or peptide, that exhibits a partial, complete, competitive and/or inhibitory effect by inhibiting, suppressing, repressing, or decreasing a specific activity, such as platelet activation or adhesion activity, stabilization of thromboses, metastasis, angiogenesis, or viral infection. In certain embodiments, the term preferably refers to an inhibitor of human pathological platelet activity, thus diminishing or blocking, preferably diminishing, some or all of the biological effects of pathological platelet activity. In certain other embodiments, the term preferably refers to an inhibitor of angiogenesis, metastasis, morphogenesis, matrix reorganization, cell migration, cell proliferation, cell colonization, or leukocyte infiltration. In still other embodiments, the term preferably refers to an inhibitor of viral infection.

The term "administering" means either directly administering a compound or composition of the present invention, or administering a prodrug, derivative or analog which will form an equivalent amount of the active compound or substance within the body.

"Dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

The term "vascular system" refers to the vessels and tissue that carry or circulate fluids in the body of an animal, including but not limited to the heart, blood vessels, lymphatic, pulmonary, and portal systems.

The phrases "vascular disease", "vascular disorder", "vascular condition", "vascular pathology", and the like, refer to bodily states affecting the channels and tissue that carry body fluids, such as, but not limited to stroke, deep vein thrombosis (DVT), myocardial infarction, coronary artery disease, cerebrovascular disease, peripheral arterial disease, diabetes mellitus, atrial fibrillation, congestive heart failure, acute coronary syndromes, stroke, pulmonary embolism, and ischaemic complications of peripheral vascular disease.

The term "angiogenesis" refers to the growth, formation, migration, infiltration, or proliferation of blood vessels.

"Piconaviridae viruses" are viruses belonging to the virus family Piconaviridae.

"Subject" or "patient" refers to an embryonic, immature, or adult animal, including the human species, that is treatable with the compositions, and/or methods of the present invention.

The disclosures of each patent, patent application, and publication cited or described in this document are hereby incorporated herein by reference, in their entirety.

The present invention is directed to, among other things, small-molecule inhibitors of the α2β1 integrin and methods of their use for the treatment of certain vascular disorders and conditions, cancers, diabetes- and arthritis-related conditions, and viral infections. Because the activity of the disclosed compounds of formulas I is attributable to α2β1 antagonism and otherwise provides inhibition of particular collagen-induced platelet activity, with respect to treatment of vascular conditions, administration thereof represents an extremely promising and heretofore unachieved strategy for safe antithrombotic therapy and treatment of other disease states associated with the vascular system. For example, it is believed that the present invention described presents a substantial breakthrough in the field of treatment, alleviation, inhibition, and/or prevention of such disorders and conditions, including, but not limited to, stroke, deep vein thrombosis (DVT), myocardial infarction, coronary artery disease, cerebrovascular disease, peripheral arterial disease, atrial fibrillation, and congestive heart failure, acute coronary syndromes, stroke, pulmonary embolism, and ischaemic complications of peripheral vascular disease. In an additional aspect, the present invention represents a promising and distinctive therapy for cancer and cancer-related conditions, including, but not limited to human melanoma, hepatocellular carcinoma, breast, lung, and ovarian cancers, pathological angiogenesis, metastasis, and leukocyte infiltration. In a still further aspect, the invention provides a means of treatment for diabetes- and arthritis-related ailments, such as rheumatoid arthritis, diabetic retinopathy, diabetes mellitus, and related conditions. Administration of the compounds of formula I also provides medicinal therapy as against viral infection, for example, by the human cytomegalovirus, rotaviruses, or Piconaviridae viruses, or susceptibility thereto.

In accordance with one embodiment of the present invention, provided are compounds having the formula I:

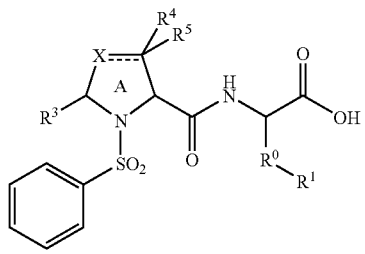

wherein:
X is alkylene, N, O, S, or $SO_2$;
$R^0$ is alkylene;
$R^1$ is —NHC(=O)$R^2$;
$R^2$ is —NH(CH$_2$)aryl;

R³ is H, alkyl, aryl, or aralkyl, or forms a three- to six-membered carbocyclic or heterocyclic ring together with X and the carbon atom to which R³ and X are both attached;

R⁴ and R⁵ are each independently H or —CH₃;

wherein the dashed line may represent a double bond;

if R⁴ and R⁵ are both H, then

X is SO₂; or,

X is S and R³ is not H; or,

X is —CH— and the dashed line represents a double bond;

and, if X is ethylidene, then one carbon atom of X, R³, and the carbon atom to which both are attached form a three- to six-membered carbocyclic or heterocyclic ring, or, X forms a fused bicycle together with Ring A;

or a stereoisomer, partial stereoisomer, prodrug, pharmaceutically acceptable salt, hydrate, solvate, acid hydrate, or N-oxide thereof.

In other embodiments, the invention is directed to pharmaceutical compositions comprising a pharmaceutically-acceptable carrier, diluent, or excipient and a compound of formula I. Other embodiments of the invention provide compositions comprising a stereochemically enriched mixture of compounds of formula I.

In other aspects, R¹ is —NHC(=O)R², X is S or O, and R³ is alkyl, aryl, or aralkyl. In accordance with such embodiments, X may be S and R⁴ and R⁵ may both be H or may both be —CH₃. Exemplary compounds of such embodiments include:

2-[(3-Benzenesulfonyl-2-methyl-thiazolidine-4-carbonyl)-amino]-3-(3-benzyl-ureido)-propionic acid;

2-[(3-Benzenesulfonyl-2-ethyl-thiazolidine-4-carbonyl)-amino]-3-(3-benzyl-ureido)-propionic acid;

2-[(3-Benzenesulfonyl-2-isopropyl-thiazolidine-4-carbonyl)-amino]-3-(3-benzyl-ureido)-propionic acid;

2-[(3-Benzenesulfonyl-2-tert-butyl-thiazolidine-4-carbonyl)-amino]-3-(3-benzyl-ureido)-propionic acid;

2-[(3-Benzenesulfonyl-2-phenyl-thiazolidine-4-carbonyl)-amino]-3-(3-benzyl-ureido)-propionic acid;

2-[(3-Benzenesulfonyl-2-phenethyl-thiazolidine-4-carbonyl)-amino]-3-(3-benzyl-ureido)-propionic acid;

2-[(3-Benzenesulfonyl-2,5,5-trimethyl-thiazolidine-4-carbonyl)-amino]-3-(3-benzyl-ureido)-propionic acid; and, 2-[(3-Benzenesulfonyl-2-ethyl-5,5-dimethyl-thiazolidine-4-carbonyl)-amino]-3-(3-benzyl-ureido)-propionic acid, among others.

In other embodiments wherein R¹ is —NHC(=O)R², X may be O, R⁴ may be H, R⁵ may be —CH₃, and R³ may be alkyl. For example, the compound may be 2-[(3-Benzenesulfonyl-2,5-dimethyl-thiazolidine-4-carbonyl)-amino]-3-(3-benzyl-ureido)-propionic acid.

When R¹ is —NHC(=O)R², R³, R⁴, and R⁵ may each be H, and X may be SO₂. For example, the compound may be 2-[(3-Benzenesulfonyl-1,1-dioxo-1λ⁶-thiazolidine-4-carbonyl)-amino]-3-(3-benzyl-ureido)-propionic acid.

In other embodiments, X is ethylidene, and either R³ forms a three- to six-membered carbocyclic or heterocyclic ring together with X and the carbon atom to which R³ and X are both attached, or X forms a fused bicycle together with Ring A. Exemplary compounds of this variety include, among others, 2-[(2-Benzenesulfonyl-1,2,3,4-tetrahydro-isoquinoline-3-carbonyl)-amino]-3-(3-benzyl-ureido)-propionic acid, and 2-[(1-Benzenesulfonyl-1,2,3,4-tetrahydro-quinoline-2-carbonyl)-amino]-3-(3-benzyl-ureido)-propionic acid.

In still other embodiments, X is —CH—, the dashed line represents a double bond, R¹ is —NHC(=O)R², R² is —NH(CH₂)phenyl, and R³, R⁴, and R⁵ are each H. For example, the compound may be 2-[(1-Benzenesulfonyl-2,5-dihydro-1H-pyrrole-2-carbonyl)-amino]-3-(3-benzyl-ureido)-propionic acid.

In another aspects, the present invention is directed to methods for treating at least one α2β1-affected disease state or infection comprising administering to a subject in need thereof a composition comprising a therapeutically effective amount of a compound having the formula I, as described above. The present methods are intended to embrace the administration of a therapeutically effective amount of any compound or compounds disclosed herein. The composition may additionally comprise a pharmaceutically acceptable carrier, diluent, or excipient. Additionally or alternatively, the composition may comprise a stereochemically enriched mixture of compounds of the formula I.

In accordance with the present methods, subject may be suffering from or susceptible to one or more of acute coronary syndromes, stroke, ischaemic complications of peripheral vascular disease, deep vein thrombosis (DVT), myocardial infarction, coronary artery disease, cerebrovascular disease, peripheral arterial disease, diabetes mellitus, atrial fibrillation, congestive heart failure, pulmonary embolism, and other vascular-related disorders that will be readily appreciated by those skilled in the art. The subject may also or alternatively be suffering from or susceptible to one or more of human melanoma, hepatocellular carcinoma, breast cancer, lung cancer, ovarian cancer, and other cancers or cancer-related disorders. Likewise, the subject may be suffering from or susceptible to one or more of rheumatoid arthritis, diabetic retinopathy, and other rheumatoid- or diabetes-related disorders.

The disease state or infection may be matrix reorganization-affected, angiogenesis-affected, cell migration-, cell proliferation-, cell colonization-, or metastasis-affected, leukocyte infiltration-affected, edema-affected, or any combination thereof.

In other embodiments, subject may be suffering from or susceptible to viral infection. The viral infection may be at least partially attributable to human cytomegalovirus (HCMV), rotaviruses, Piconaviridae viruses, or related viruses.

The compounds employed in the present invention may exist in prodrug form. As used herein, "prodrug" is intended to include any covalently bonded carriers which release the active parent drug, for example, as according to the formulas or compounds employed in the methods of the present invention in vivo when such prodrug is administered to a subject. Since prodrugs are known to enhance numerous desirable qualities of pharmaceuticals (e.g., solubility, bioavailability, manufacturing, etc.) the compounds of the present invention may, if desired, be delivered in prodrug form. Thus, the present invention contemplates methods of delivering prodrugs. Prodrugs of the compounds employed in the present invention, for example, according to formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tent-butyl, cyclopropyl, phenyl, benzyl, and phenethyl esters, and the like.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T W. and Wuts, P. G. M., *Protective Groups in Organic Synthesis 2d. Ed.*, Wiley & Sons, 1991.

In a further aspect, the invention relates to a pharmaceutical composition comprising a compound of formula I and a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety.

The compounds of this invention may be administered orally or parenterally, neat or in combination with conventional pharmaceutical carriers, diluents, or excipients, which may be liquid or solid. The applicable solid carrier, diluent, or excipient may function as, among other things, a binder, disintegrant, filler, lubricant, glidant, compression aid, processing aid, color, sweetener, preservative, suspending/dispersing agent, tablet-disintegrating agent, encapsulating material, film former or coating, flavors, or printing ink. Of course, any material used in preparing any dosage unit form is preferably pharmaceutically pure and substantially non-toxic in the amounts employed. In addition, the active compound may be incorporated into sustained-release preparations and formulations. Parenteral administration in this respect includes administration by, inter alia, the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol, and rectal systemic.

In powders, the carrier, diluent, or excipient may be a finely divided solid that is in admixture with the finely divided active ingredient. In tablets, the active ingredient is mixed with a carrier, diluent or excipient having the necessary compression properties in suitable proportions and compacted in the shape and size desired. For oral therapeutic administration, the active compound may be incorporated with the carrier, diluent, or excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. The therapeutic compositions preferably contain up to about 99% of the active ingredient.

Liquid carriers, diluents, or excipients may be used in preparing solutions, suspensions, emulsions, syrups, elixirs, and the like. The active ingredient of this invention can be dissolved or suspended in a pharmaceutically acceptable liquid such as water, an organic solvent, a mixture of both, or pharmaceutically acceptable oils or fat. The liquid carrier, excipient, or diluent can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators.

Suitable solid carriers, diluents, and excipients may include, for example, calcium phosphate, silicon dioxide, magnesium stearate, talc, sugars, lactose, dextrin, starch, gelatin, cellulose, methyl cellulose, ethylcellulose, sodium carboxymethyl cellulose, microcrystalline cellulose, polyvinylpyrrolidine, low melting waxes, ion exchange resins, croscarmellose carbon, acacia, pregelatinized starch, crospovidone, HPMC, povidone, titanium dioxide, polycrystalline cellulose, aluminum methahydroxide, agar-agar, tragacanth, or mixtures thereof.

Suitable examples of liquid carriers, diluents and excipients for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil), or mixtures thereof.

For parenteral administration, the carrier, diluent, or excipient can also be an oily ester such as ethyl oleate and isopropyl myristate. Also contemplated are sterile liquid carriers, diluents, or excipients, which are used in sterile liquid form compositions for parenteral administration. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier, diluent, or excipient may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient or ingredients, plus any additional desired ingredient from the previously sterile-filtered solution thereof.

The compounds of the invention may be administered in an effective amount by any of the conventional techniques well-established in the medical field. The compounds employed in the methods of the present invention including, for example, the compounds of formula I may be administered by any means that results in the contact of the active agents with the agents' site or sites of action in the body of a patient. The compounds may be administered by any conventional means available.

Preferably the pharmaceutical composition is in unit dosage form, e.g. as tablets, buccal tablets, troches, capsules, elixirs, powders, solutions, suspensions, emulsions, syrups, wafers, granules, suppositories, or the like. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form. In addition, dosage forms of the present invention can be in the form of capsules wherein one active ingredient is compressed into a tablet or in the form of a plurality of microtablets, particles, granules or non-perils. These microtablets, particles, granules or non-perils are then placed into a capsule or compressed into a capsule, possibly along with a granulation of the another active ingredient.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The dose may also be provided by controlled release of the compound, by techniques well known to those in the art.

The compounds useful in the methods of the present invention may be prepared in a number of ways well known to those skilled in the art. The compounds can be synthesized, for example, by the methods as described below, or variations thereon as appreciated by the skilled artisan. The reagents used in the preparation of the compounds of this invention can be either commercially obtained or can be prepared by standard procedures described in the literature. All processes disclosed in association with the present invention are contemplated to be practiced on any scale, including milligram, gram, multigram, kilogram, or commercial industrial scale.

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Increasing the Affinity of Pro-Dap $\alpha_2\beta_1$ Antagonists

Selective small molecule $\alpha_2\beta_1$ inhibitors were developed, based on a 2,3-diaminopropionic acid (Dap) backbone[21]:

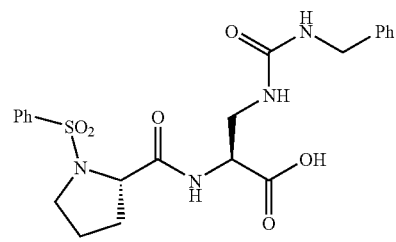 [SMILES: O=C(NCc1ccccc1)NC[C@H](NC(=O)[C@@H]1CCCN1S(=O)(=O)c1ccccc1)C(=O)O]

The design of these antagonists were based in part on $\alpha_4\beta_1$ inhibitors incorporating a benzenesulfonyl-prolyl-phenylalanine (Pro-Phe) scaffold[22-24]

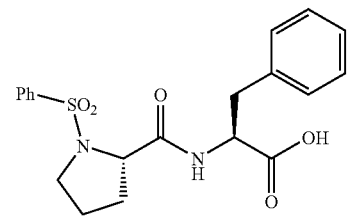 [SMILES: O=C(O)[C@H](Cc1ccccc1)NC(=O)[C@@H]1CCCN1S(=O)(=O)c1ccccc1]

and $\alpha_{IIb}\beta_3$ Inhibitors Containing a 2,3-diaminopropionic Acid (Dap) Moiety[25-26]

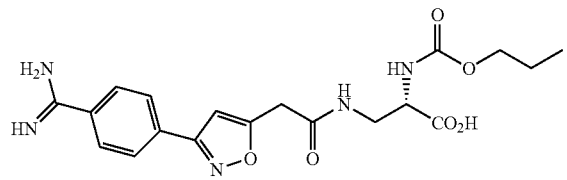 [SMILES: CCCOC(=O)N[C@@H](CNC(=O)Cc1cc(-c2ccc(C(=N)N)cc2)no1)C(=O)O]

However, the most potent of the previously synthesized compounds failed to show good activity in vivo. A number of structural modifications were investigated to improve the potency. The conformation and physicochemical properties of the Pro residue were systematically varied using a series of Pro surrogates as depicted in Scheme 1:

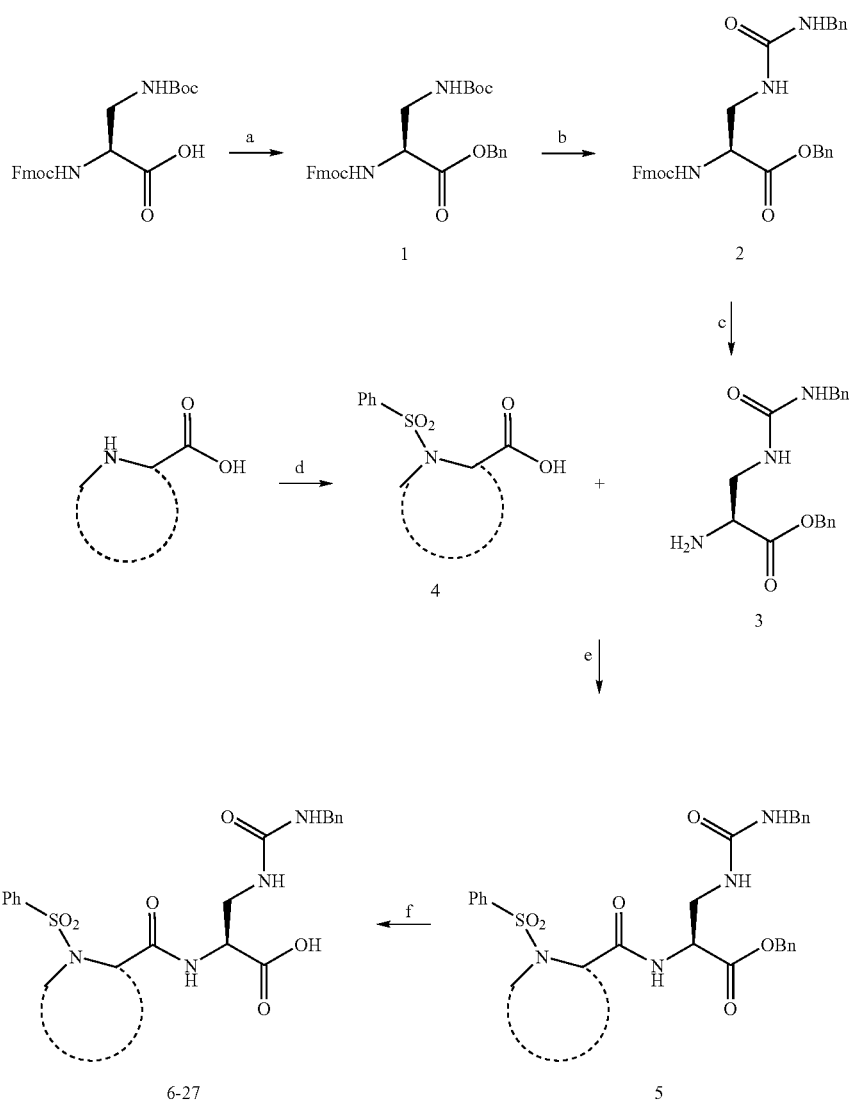

Reagents and conditions for Scheme 1 were as follows: (a) BnBr, NaHCO$_3$, DMF; (b) (i) TFA, CH$_2$Cl$_2$; (ii) i-Pr$_2$EtN, BnNCO, DMF; (c) Et$_2$NH, CH$_2$Cl$_2$; (d) PhSO$_2$Cl, NaHCO$_3$, DMF/H$_2$O; (e) HATU, HOAt, i-Pr$_2$EtN, DMF; (f) for sulfur containing heterocycles: BCl$_3$, CH$_2$Cl$_2$; for oxygen containing heterocycles: Pd/C, H$_2$, MeOH.

The ability of these compounds to inhibit platelet adhesion to type I collagen was evaluated. Table 1, below, depicts compounds that were investigated to establish the role of the heterocycle in determining potency:

TABLE 1

| Compound | X | IC$_{50}$ (nM) |
|---|---|---|
| 6 | 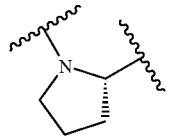 | 67 |

TABLE 1-continued

[Structure shown: Ph-S(O2)-X-C(O)-NH-CH(COOH)-CH2-NH-C(O)-NH-CH2-Ph]

| Compound | X | IC$_{50}$ (nM) |
|---|---|---|
| 7 | HN-cyclopentyl (spiro) | >1,000 |
| 8 | HN-cyclohexyl (spiro) | >1,000 |
| 9 | 2,5-dihydropyrrole | 60 |
| 10 | azetidine | 215 |
| 11 | piperidine | 64 |
| 12 | tetrahydroisoquinoline | >1,000 |
| 13 | tetrahydroquinoline | 127 |

Altering the Pro in the parent compound (6) to a desaturated Pro analogue, dehydroproline (9), retained the activity of the parent compound, as did an analogue in which the five-membered ring was expanded to a six-membered piperidine (11). Contracture of the ring to an azetidine (10) or inclusion of fused rings as in the tetrahydroquinoline derivatives (12-13) decreased activity. Various other analogues (7-8) also led to loss of potency. However, alteration of Pro to thiazolidine (compound 14) significantly increased activity.

Other substituted 5-membered heterocycles were investigated. Table 2, below, depicts the investigated compounds:

TABLE 2

[Structure shown: Ph-SO2-N(ring with X, R1, R2, R3)-C(O)-NH-CH(COOH)-CH2-NH-C(O)-NH-CH2-Ph]

| Compound | X | R$^1$ | R$^2$ | R$^3$ | IC$_{50}$ (nM) |
|---|---|---|---|---|---|
| 6 | CH$_2$ | H | H | H | 67 |
| 14 | S | H | H | H | 17 |
| 15 | S | Me | Me | H | 12 |
| 16 | S | H | H | Me | 6 |
| 17 | S | H | H | Et | 49 |
| 18 | S | H | H | i-Pr | 958 |
| 19 | S | H | H | i-Bu | >1,000 |
| 20 | S | H | H | Ph | >1,000 |
| 21 | S | H | H | CH$_2$CH$_2$Ph | 740 |
| 22 | S | Me | Me | Me | 180 |
| 23 | S | Me | Me | Et | 170 |
| 24 | S(O)$_2$ | H | H | H | 227 |
| 25 | O | H | H | H | 82 |
| 26 | O | H | Me | H | 12 |
| 27 | O | H | Me | Me | 25 |

Addition of a gem dimethyl substitution at the 5-position (15) improved activity slightly over the thiazolidine parent compound (14). Improvement was also observed by addition of a methyl substituent at the 2-position (16). Substitution of larger, sterically demanding groups (17-21) decreased potency. A combination of the potency-enhancing structural features of compounds 15 and 16 was made, which might have been expected to provide an additive benefit; instead this combination of substituents led a dramatic loss in activity (22). Replacing the thioether with a sulfone (24) or an ether (25-27) also decreased potency, possibly due to an increase in the polarity of the compounds.

Example 2

Computational Studies of the $\alpha_2\beta_1$ Antagonist Binding to the $\beta_1$ I-Like Domain Substituents in Pro analogues have an important effect on their conformational properties, which in turn strongly affect the energetics of ligands interacting with their receptors.[27-28] Thus, the preferred conformations of the Pro analogue in the potent compounds 15 and 16 were examined, versus the less potent compound 22, which combined the substitutions in 15 and 16. This set of compounds was chosen because their structures differ by only a single methyl group. The pyrrolidine ring of Pro derivatives can assume two conformations with an UP (C$^\gamma$-exo) or a DOWN (C$^\gamma$-endo) pucker, based on the relationship between the γ-position ring atom (the thioether in this case) and the carbonyl group.[29] In the exo conformation, the γ atom and the carbonyl group are on opposite sides of the plane, while they are on the same side of the plane in the endo conformation. The crystal structure of a fragment of 16 confirmed the stereochemistry of the compound and also showed that the substitution at the 2-position stabilized the thiazolidine ring in the exo conformation, placing the carbonyl in a gauche relationship relative to the γ-thioether. This conformation is less stable than the endo conformation in unsubstituted Pro analogues,[27] suggesting (without intending to be bound by any particular theory of operation) that this conformation might be important for activity.

Figure 2:
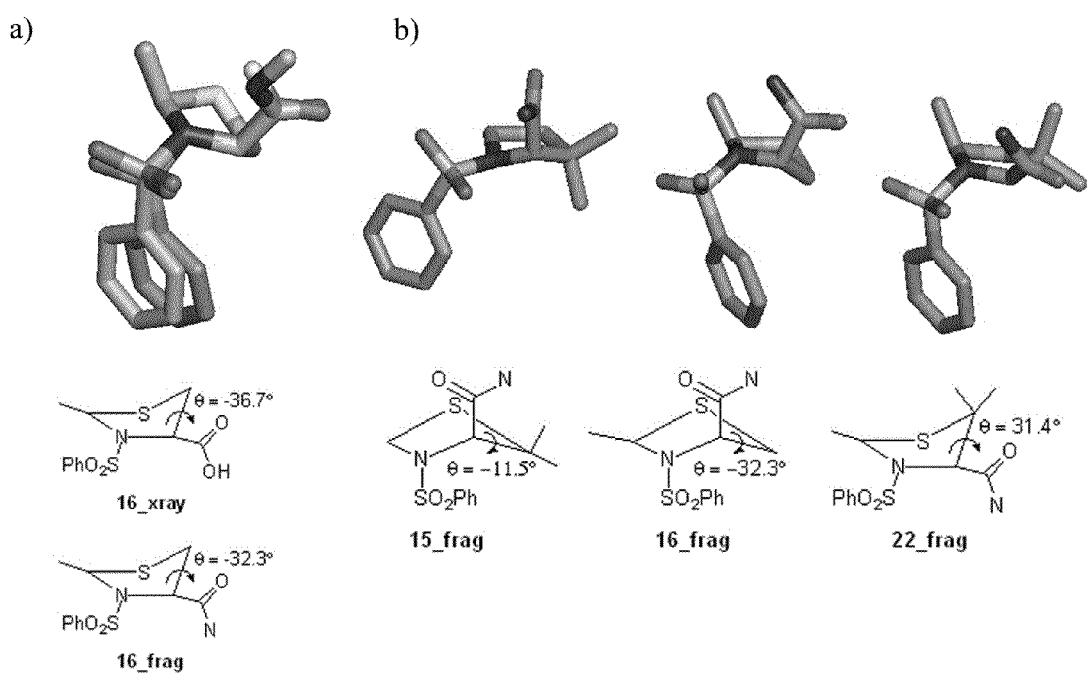
FIG. 2 shows (A) single crystal x-ray structure for the carboxylic acid derivative of compound 16 overlaid with the calculated structure for the amide derivative of 16; and, (B) a comparison of the calculated structure for active inhibitors 15_frag and 16_frag with inactive inhibitor 22_frag

Supporting this possibility, quantum mechanical calculations also identified the same minimum-energy conformation, shown overlaid with the crystal structure in FIG. 2a, which shows the single crystal x-ray structure for the carboxylic acid derivative of 16 (16_xray) overlaid with the calculated structure for the amide derivative of 16 (16_frag). The energy-minimized model is in excellent agreement with the experimentally-derived crystal structure, as illustrated by the similarity in the $\Psi_2$ angles.

The same three-dimensional structure was found for the prolyl-sulfonamide fragment in 15; FIG. 2b provides a comparison of the calculated structure for active inhibitors 15_frag and 16_frag with inactive inhibitor 22_frag. The substituents on 22 force the five-membered ring into the exo conformation (positive $\Psi_2$) while 15 and 16 assume the more favorable endo conformation (negative $\Psi_2$). The amide assumes a pseudo-equatorial position in 22 and a pseudo-axial position in 15 and 16. The presence of three methyl substituents in 22 force this compound into the endo conformation with a trans relationship between the carbonyl carbon and thioether sulfur atom.

Figure 3:
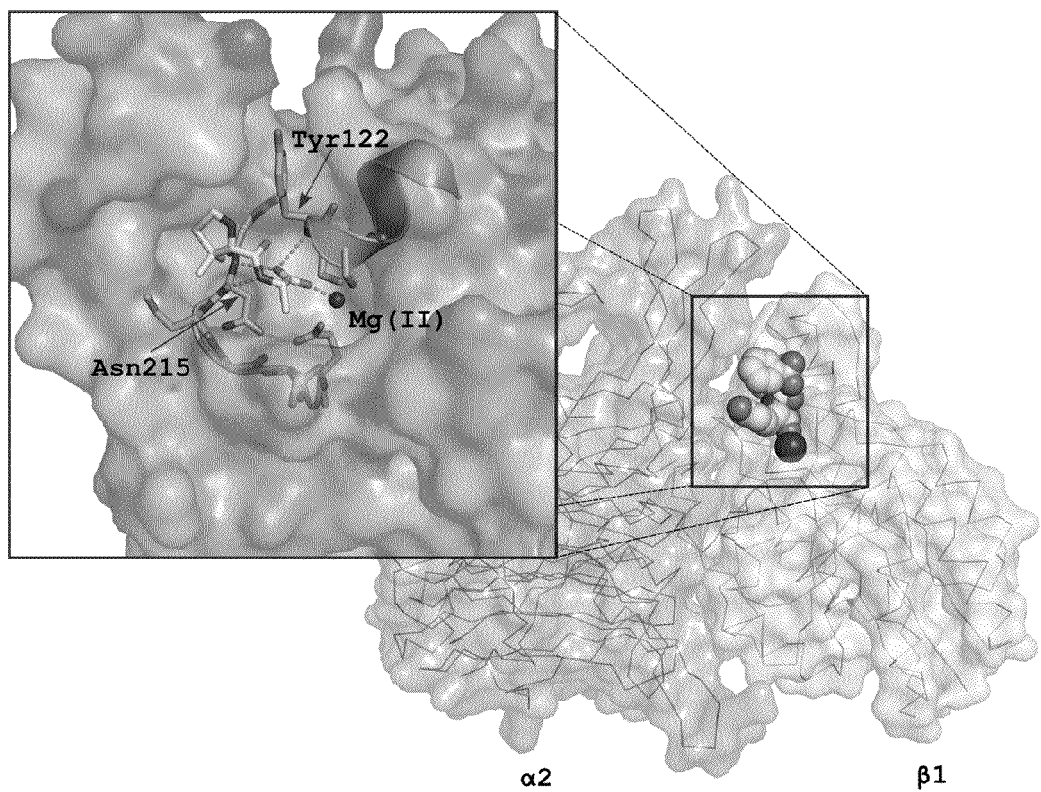
FIG. 3 depicts the inhibitor scaffold (thiazolidine-containing dipeptide mimetic) docked into the binding site on the model of the $\beta_1$ integrin.

A crystallographic structure of the intact α2β1 integrin is not available, and so a model was constructed based on the three-dimensional structure of the $\alpha_{IIb}\beta_3$ extracellular domains and the known three-dimensional structure of the $\alpha_2\beta_1$ I-domain.[10-30] To further understand the structure-activity relationships, compound 15 was docked onto a model of the relevant regions of the $\alpha_2\beta_1$ extracellular domains. FIG. 3 depicts the inhibitor scaffold (thiazolidine-containing dipeptide mimetic) docked into the binding site on the model of the $\beta_1$ integrin. The Mg$^{2+}$ is coordinated by polar groups from $\beta_1$ and the terminal carboxylate of the inhibitor. The $\beta_1$ integrin provides three well-positioned backbone polar atoms coming from the end of an α-helix (Tyr122) and a tight turn (Asn215) that help lock the inhibitor into the binding site. The thiazolidine ring binds into the opening of a hydrophobic pocket, showing nice shape complementarity. The hydrophobic character and the restrictive size of this pocket help explain the allowable substitutions on the thiazolidine ring. There was excellent homology between the $\beta_1$ integrin and the template $\beta_3$ integrin around this binding site, save for the hydrophobic pocket which does not exist on the $\beta_3$ surface. The limited homology between the sequences of $\alpha_2$ and $\alpha_{IIb}$ in this binding region precluded a more detailed analysis of the interactions between the inhibitors and the α subunit. For clarity some of the surfaces near the Mg$^{2+}$ have been removed.

Inhibitors of $\alpha_{IIb}\beta_3$ and $\alpha_v\beta_3$ bind at a site between the α and β subunits, invariantly forming an interaction with a divalent cation in the β-chain I-like domain.[31] In I-domain-containing integrins, a carboxylate-containing side chain (Glu336 in α$_2$ integrins) binds to this metal ion, stabilizing the activated conformation of the integrin.[14] Antagonists of I-domain-containing integrins have been proposed to bind to this site, the I-like domain, locking the integrin in the inactive conformation.[31] Thus, compound 15 docks into the homology model in a geometry appropriate for interaction with the Mg$^{2+}$ ion.

The I-like domain in $\alpha_2\beta_1$ has a number of notable features (FIG. 3) that help explain the SAR and the specificity of our antagonists for integrin $\alpha_2\beta_1$ over other $\beta_1$ integrins.[21] For example, the pocket in $\beta_1$ is unable to accommodate the large bicyclic Pro analogue 12 or bulky substituents at the 2-position of the thiazolidine ring, explaining the lack of potency observed in these inhibitors. In addition, the urea moiety of the Dap side chain projects towards the α$_2$ subunit, explaining the specificity of this class of compounds for $\alpha_2\beta_1$ versus other $\beta_1$ integrins (see below).[21]

The present inventors have previously shown that Pro-Dap-based inhibitors do not inhibit binding of isolated α$_2$ I-domains in vitro to type I collagen, suggesting that they inhibit adhesion indirectly by binding to the β subunit and preventing activation.[21] To investigate this possibility, the ability of the present inhibitors to block cell adhesion to collagen using mutants of $\alpha_2\beta_1$ transfected in RBL hematopoietic cells was investigated. A constitutively activated mutant E318A (pictured in FIG. 1) in the α$_2$ chain of the full-length integrin was first investigated.[32] This mutant disrupts a salt bridge in the I-domain that is critical to the stability of the "closed" conformation of the integrin, bypassing the requirement for an interaction between the α$_2$ I-domain and the $\beta_1$ I-like domain to achieve the activated conformation.[14, 33] It was predicted that the present compounds would not inhibit adhesions of cells bearing this mutation to collagen surfaces. To test this hypothesis we first measured the ability of compound 15 to inhibit adhesion of RBL cells bearing wild-type integrin $\alpha_2\beta_1$ to collagen. Compound 15 therefore inhibits adhesion with an IC$_{50}$ approximately five to ten-fold higher than for static platelet adhesion, probably reflecting differences in integrin density and/or a greater activation state of $\alpha_2\beta_1$ in RBL cells. By contrast, compound 15 has no affect on adhesion of the constitutively active mutant E318A (IC$_{50}$>10 µM), confirming that this mutation acts by inducing a constitutively active conformation in the α$_2$ I-domain.

To further test the activation mechanism and to determine whether these compounds would be effective under conditions that mimic strong activation via "inside-out" signaling pathways, the effect of these antagonists on the deletion of GFFKR in the cytoplasmic tail of α$_2$ was studied.[11, 12] Deletion of GFFKR is a well-known way to induce integrin activation through the normal platelet activation pathway (FIG. 1).[34, 35] In this case, the extracellular domains of $\alpha_2\beta_1$ remain intact but the equilibrium is shifted towards the activated state by mutation of the cytoplasmic domain. Compound 15 should still be able to inhibit this mutant by blocking the I-domain-binding site in the $\beta_1$ I-like domain, although this inhibitor might not be as potent because Del (GFFKR) indirectly shifts the equilibrium to the activated state.

Figure 4:
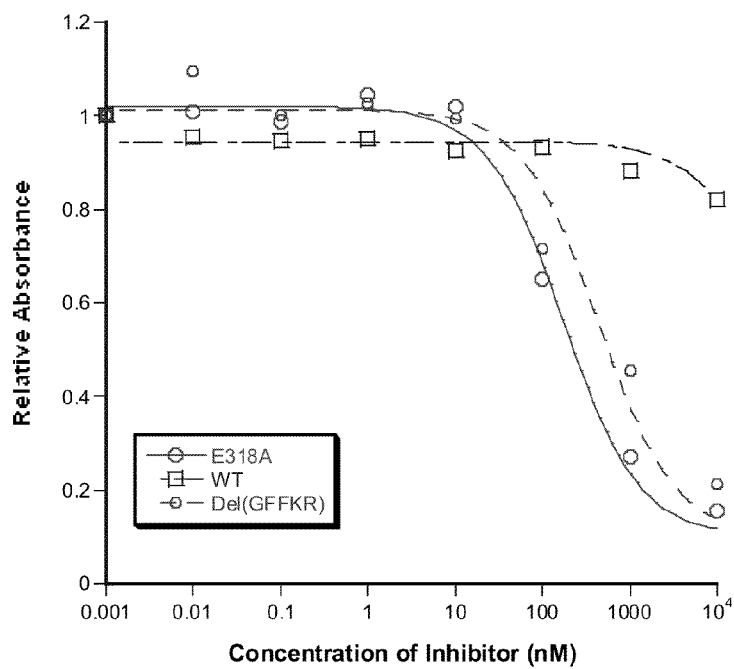
FIG. 4 illustrates the results of a study of the adhesion of $\alpha_2\beta_1$-expressing RBL cells to type I collagen under static conditions.

FIG. 4 illustrates the results of a study of the adhesion of $\alpha_2\beta_1$-expressing RBL cells to type I collagen under static conditions. Compound 15 inhibits adhesion of cells expressing wild-type (WT) demonstrates no effect on RBL cells expressing an activating I-domain mutation (E318A) but inhibits an activating cytoplasmic domain mutant (Del(G-FFKR)) with an IC$_{50}$ approximately four-fold higher than for wild-type integrin $\alpha_2\beta_1$ (WT). The IC$_{50}$ for WT and Del (GFFKR) varied approximately two-fold on different assay days but the relative potency of compound for the mutants remained constant. Together, these data suggest (without intending to be bound by any particular theory of operation) that 15 inhibits adhesion by interrupting the interaction of the α$_2$ I domain with the $\beta_1$ I-like domain; this compound has no affect on adhesion cells bearing a mutant (E318A) that bypasses the need for alpha-beta interactions to achieve the activated state, whereas 15 is fully active but has decreased potency when measured with cells bearing Del(GFFKR), which enhances the normal activation via the pathway shown in FIG. 1.

Example 3

Demonstration that Pro-Dap-Based Compounds Bind Specifically to $\alpha_2\beta_1$ Platelets express five integrins which bind to ligands in the extracellular matrix. $\alpha_{IIb}\beta_3$, $\alpha_v\beta_3$, $\alpha_2\beta_1$, $\alpha_5\beta_1$, and $\alpha_6\beta_1$.[36] A study was conducted as to the ability of several compounds (15, 16, and 25) to block platelet binding to the ligands of these other integrins to assess specificity. To examine $\alpha_5\beta_1$-mediated adhesion, the ability of platelets to adhere to fibronectin-coated surfaces in the presence of abciximab (the human-murine monoclonal antibody to $\beta_3$ integrins to control for $\alpha_{IIb}\beta_3$- and $\alpha_v\beta_3$-mediated platelet adhesion to fibronectin) was measured.[36] As expected, it was found that our compounds had no effect on binding at concentrations exceeding 1000 nM. To assess $\alpha_v\beta_3$-mediated adhesion, the ability of the compounds to inhibit ADP-stimulated platelet adhesion to osteopontin was measured.[37] Again, no effect was observed at compound concentrations greater than 1000 nM. Similarly, the compounds had no effect on ADP-stimulated platelet aggregation, an integrin $\alpha_{IIb}\beta_3$-mediated process, at concentrations as great as 20 µM.

Example 4

Demonstration that Pro-Dap-Based $\alpha_2\beta_1$ Antagonists Inhibit Arterial Thrombosis in Mice Normal blood flow concentrates platelets near the vessel wall where they can interact with the endothelium and sub-endothelial matrix proteins. In vascular diseases such as atherosclerosis, the blood vessels are narrowed, which increases the shear stress on platelets and promotes high-shear platelet activation. To replicate this pathological process, a study was undertaken of the ability of three representative compounds to block platelet adhesion to fibrillar collagen under flow at 1000 s$^{-1}$, a condition chosen to mimic platelet function in vivo. Two of the most potent compounds, 15 and 16 (12 and 6 nM under static conditions, respectively) remained similar under flow (715 nM and 698 nM). The IC$_{50}$ for 6 (67 nM under static conditions) increased to 3.6 µM under flow conditions. Although the relative efficacy of the compounds remained approximately the same, the IC$_{50}$ of each compound increased when compared to static platelet adhesion, an observation which could explain the difference in in vivo efficacy between 15 and 6.

Figure 5:
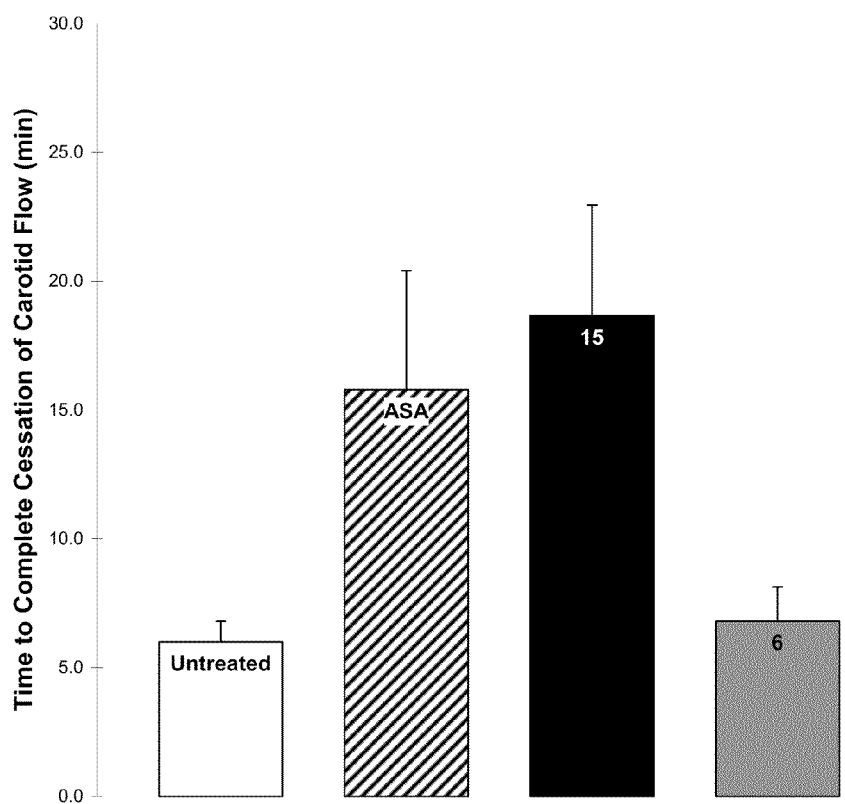
FIG. 5 provides the results of a study designed to determine total time to occlusion (TTO) following ferric chloride-induced carotid artery injury in mice in order to assess the ability of inventive compounds to prevent thrombosis in vivo.

To test further the potential of these inhibitors as antithrombotic agents in vivo, the present inventors examined the ability of the compounds to inhibit thrombus formation in a mouse model of arterial damage. The total time to occlusion (TTO) following ferric chloride-induced carotid artery injury after administration of compound 6 or 15 was measured[38, 39]; results are shown in FIG. 5. Wild-type C57BL/6J mice were intravenously given vehicle (200 µL PBS) (n=5), aspirin (10 mg/kg) (n=6), or the integrin $\alpha_2\beta_1$ inhibitor (6 or 15, 60 mg/kg, n=9 for 15 and n=6 for 6) intravenously 15 minutes prior to the assay. The aspirin was administered at a dose that has been shown to abolish thromboxane A$_2$ generation)[40] or vehicle was positive and negative controls. The carotid artery was surgically exposed, injured with 10% ferric chloride solution for 2.5 minutes, and then washed with PBS. Blood flow through the carotid artery was measured for 30 minutes via a Doppler ultrasound probe. Statistical analysis was performed using one-way ANOVA analysis relative to sham-treated controls (* p=0.09,  p=0.04, * p=0.62). Compound 15 delayed clot formation by three-fold (TTO=18.7±12.2 min, p=0.04 compared to 6.0±1.8 min sham-treated mice), similar to the efficacy of aspirin (TTO=15.8±11.3 min). By contrast, the less potent compound 6 had no effect on TTO (6.8±3.0 minutes, p=0.62).

Interaction between circulating platelets and collagen at sites of vascular injury plays a critical role in pathological thrombus formation. A modified prolyl-2,3-diaminopropionic acid (Pro-Dap) scaffold has been employed in order to synthesize a series of small molecule inhibitors that potently and selectively block integrin $\alpha_2\beta_1$ binding to type I collagen. These small molecule antagonists represent the first compounds targeting $\alpha_2\beta_1$ to demonstrate in vivo efficacy in a model of pathological thrombosis. The efficacy of the present agents is consistent with observations of $\alpha_2$-null mice that suggest integrin $\alpha_2\beta_1$ plays a role in thrombus growth and stabilization.[40]

These compounds are not only useful as antithrombotic agents and inhibitors of other $\alpha_2\beta_1$-effected disease states and infections, but also have helped elucidate the biology of the integrin. The disclosed computational model for integrin $\alpha_2\beta_1$ is consistent with the mode of binding and demonstrates the mechanism for selectivity among $\beta_1$ integrins with different $\alpha$ partners. The urea sidechains attached to the Dap portion of the scaffold project towards the $\alpha_2$ chain, which could explain the selectivity of this class of inhibitors for $\alpha_2\beta_1$ over the structurally related integrin $\alpha_4\beta_1$.[21] This observation establishes the $\beta/\beta$ interface as an excellent target for obtaining highly selective inhibitors of the $\beta_1$ family. Finally, these studies extend and confirm previous suggestions of the mechanism of integrin activation and the mode of binding of this class of inhibitors to the I-domain-containing class of integrins.

Example 5

Materials and Methods

Blood Collection & Preparation of Gel-Filtered Platelets.

All studies were conducted following IRB-approved protocols. Human blood was collected by venipuncture from healthy volunteers using sodium citrate as an anticoagulant. Platelet-rich plasma (PRP) was prepared by centrifuging whole blood (200 g, 20 min). The PRP was carefully removed and applied to a Sepharose CL-2B column (bed volume 60 cc; 11×3 cm) in GFP buffer (4 mM HEPES (pH 7.4), 135 mM NaCl, 2.7 mM KCl, 3.3 mM PO$_4$, 0.35% BSA, 0.1% glucose and 2 mM MgCl$_2$).[41] Following gel purification, the platelets were counted and diluted to the appropriate final concentration (2-3×10$^8$ platelets/mL).

Adhesion Assays and Platelet Aggregation.

Immulon 2 flat bottom 96-well plates (Dynatech Labs, Burlington Mass.) were coated with soluble type I collagen (Coll), fibronectin (FN) or osteopontin (OPN) (5 µg/ml) for 48 hrs at 4° C. The proteins were dissolved in either 5% aqueous acetic acid or 50 mM NaHCO$_3$ containing 150 mM NaCl, pH 8. The plates were washed and blocked with BSA (5 mg/ml in PBS) for at least 24 hrs. Adhesion assays using Coll and FN contained test compound and 1.6×10$^7$ platelets in GFP buffer in a final volume of 100 µl. OPN binding was assessed in a similar manner, except the platelets were incubated with 10 µM ADP (10 min, 20° C.) prior to ligand exposure and assays contained 2.4×10$^7$ platelets per well. The plates were incubated (37° C., 30 min) and washed with TBS (10 mM Tris (pH 7.4), 150 mM NaCl) (11, 21). Adherent platelets were determined by staining for acid phosphatase by addition of 5 mM p-nitrophenyl phosphate in 0.1 M sodium citrate (pH 5.4), 0.1% Triton X-100 (100 μl/well) and incubated (30 min at 37° C.).[42] Plates were developed by the addition of 50 μl 2N NaOH and read at 405 nm in a microplate reader. To assess platelet aggregation, purified platelets were incubated with $Ca^{2+}$ and fibrinogen in the presence or absence of antagonist. Next, ADP was added and aggregation was determined in a Chronolog Aggregometer (Havertown, Pa.).[41, 43] RBL cells expressing wild-type integrin $\alpha_2\beta_1$ or the constitutively activating mutations E318A or Del(GFFKR) were obtained as a generous gift from Dr. Mark L. Kahn (University of Pennsylvania). Collagen adhesion assays were performed as described above for platelet adhesion. EDTA was used as a negative control.

Flow Assays[19].

Glass coverslips were incubated with a suspension of fibrillar collagen (100 μg/mL) overnight at 4° C. Surfaces were then blocked with denatured BSA (5 mg/mL) for 1 hr at room temperature, and this was followed by subsequent washing with $NaCl/P_i$ before use in spreading assays. Coverslips were assembled onto a flow chamber (Glyotech, Gaithersburg Md.) and mounted on the stage of an inverted microscope (Zeiss Axiovert 200M). PPACK (40 μM) anticoagulated whole blood was perfused through the chamber for 3 min at a wall shear rate of $1000\ s^{-1}$, and this was followed by washing for 4 min at the same shear rate with modified Tyrodes buffer and imaged using DIC microscopy.

Computational Studies.

The molecules 15_frag, 16_frag, and 22_frag were subjected to the conformer distribution routine using the MMF-Faq forcefield, as implemented in PC Spartan 06 V101 (Wavefunction, Irvine Calif.). Geometry optimizations were performed with restricted Hartree Fock SCF (self-consistent field) calculations using the 631G* basis set for the lowest energy conformers obtained from the conformer distribution routine. For the SCF model, the restricted Hartree Fock calculations were performed using Pulay DIIS and Geometric Direct minimization. Aqueous solvation energies were calculated from SM5 models. All 3 molecules studied, 15_frag, 16_frag, and 22_frag, were fit to the experimentally derived single crystal structure for 16_xray using the Fit Atom routine implemented in Sybyl (Tripos, St. Louis Mo.). The atoms from the thiazolidine ring chosen for fitting in the Fit Atom routine were: S-1, C-2, N-3, and C-5). Structures of the integrin $\alpha_2\beta_1$ were generated through homology modeling from structures of integrin $\alpha_{IIb}\beta_3$ including 1AOX (non-collagen bound) and 1DZI (collagen-bound).[9, 10] Rosetta Dock was used to dock the generated $\alpha_2$ structure onto the $\beta_1$ homology model. Missing residues 316-338 of helix $\alpha_2$ were completed in the model using other high-resolution protein structures in the PDB database.

Thrombosis Assay[38].

All animal studies were approved by the Institutional Animal Care and Use Committee of the University of Pennsylvania. Wild-type C57BL/6J mice (Jackson Laboratories, Bar Harbor Me.) were anesthetized with pentobarbital (90 mg/kg) by intraperitoneal injection. The mice were administered vehicle (200 μL PBS), aspirin (10 mg/kg dissolved in 200 μL PBS), or the integrin $\alpha_2\beta_1$ inhibitor (60 mg/kg dissolved in 200 μL PBS) intravenously 15 minutes prior to the assay. The anesthetized animals were placed on a 37° C. warming pad throughout the experiment. The right carotid artery was exposed by blunt dissection with minimal blood loss and a miniature Doppler flow probe was attached to the artery to monitor blood flow continuously. Thrombus formation was subsequently induced by application of filter paper (1×1 mm) saturated with 10% $FeCl_3$ solution to the exposed artery in contact with the adventitial surface. After 2.5 minutes, the filter paper was removed and the vessel was washed with PBS. The blood flow was monitored continuously for 30 minutes after injury. Immediately following the experiment, the mice were sacrificed by cervical dislocation while still under deep anesthesia.

Statistics and Data Analysis.

The results obtained from adhesion assays were fitted to: m1+(m2−m1)/(1+(M0/m3)^m4), where m1=background binding, m2=maximal binding, m3=$IC_{50}$ (nM) and m4=cooperativity, using KaleidaGraph (Synergy software). The results presented are those obtained from a minimum of two independent experiments. This assay gave reproducible results for adhesion. While we observed differences in the $IC_{50}$ values between different donors, the relative potency of the compounds remained the same. For compound 15, which was included as positive control reference in all assays, the calculated $IC_{50}$ value was 12 nM+/−8 (n=18).

1. Ruggeri, Z. M. Platelets in atherothrombosis. *Nat Med* 8, 1227-1234 (2002).
2. Kritzik, M. et al. Nucleotide polymorphisms in the alpha2 gene define multiple alleles that are associated with differences in platelet alpha2beta1 density. *Blood* 92, 2382-2388 (1998).
3. Nieuwenhuis, H. K., Akkerman, J. W. N., Houdijk, W. P. M. & Sixma, J. J. Human blood platelets showing no response to collagen fail to express surface glycoprotein Ia. *Nature* 318, 470-472 (1985).
4. Nieuwenhuis, H. K., Sakariassen, K. S., Houdijk, W. P., Nievelstein, P. F. & Sixma, J. J. Deficiency of platelet membrane glycoprotein Ia associated with a decreased platelet adhesion to subendothelium: a defect in platelet spreading. *Blood* 68, 692-695 (1986).
5. Kehrel, B. et al. Deficiency of intact thrombospondin and membrane glycoprotein Ia in platelets with defective collagen-induced aggregation and spontaneous loss of disorder. *Blood* 71, 1074-1078 (1988).
6. Handa, M. et al. Platelet unresponsiveness to collagen: involvement of glycoprotein Ia-IIa (alpha2beta1 integrin) deficiency associated with a myeloproliferative disorder. *Thromb. Haemost.* 73, 521-528 (1995).
7. Nieswandt, B. & Watson, S. P. Platelet-collagen interaction: is GPVI the central receptor? *Blood* 102, 449-461 (2003).
8. Shimaoka, M. & Springer, T. A. Therapeutic antagonists and conformational regulation of integrin function. *Nat Rev Drug Discov* 2, 703-716 (2003).
9. Emsley, J., Knight, C. G., Farndale, R. W., Barnes, M. J. & Liddington, R. C. Structural basis of collagen recognition by integrin alpha2beta1. *Cell* 101, 47-56 (2000).
10. Emsley, J., King, S. L., Bergelson, J. M. & Liddington, R. C. Crystal structure of the I-domain from integrin alpha2beta1. *J. Biol. Chem.* 273, 28512-28517 (1997).
11. Jung, S. M. & Moroi, M. Signal-transducing mechanisms involved in activation of the platelet collagen receptor integrin alpha2beta1. *J. Biol. Chem.* 275, 8016-8026 (2000).
12. Takagi, J., Petre, B. M., Walz, T. & Springer, T. A. Global conformational rearrangements in integrin extracellular domains in outside-in and inside-out signaling. *Cell* 110, 599-611 (2002).
13. Lu, C., Shimaoka, M., Zang, Q., Takagi, J. & Springer, T. A. Locking in alternate conformations of the integrin alphaLbeta2 I domain with disulfide bonds reveals functional relationships among integrin domains. *PNAS* 98, 2393-2398 (2001).

14. Connors, W. L. et al. Two synergistic activation mechanisms of integrin alpha2beta1 integrin-mediated collagen binding. *J. Biol. Chem.* 282, 14675-14683 (2007).
15. Shimaoka, M. et al. Structures of the alphaL I domain and its complex with ICAM-1 reveal a shape-shifting pathway for integrin regulation. *Cell* 112, 99-111 (2003).
16. Shimaoka, M., Salas, A., Yang, W., Weitz-Schmidt, G. & Springer, T. A. Small molecule integrin antagonists that bind to the beta2 subunit I-like domain and activate signals in one direction and block them in the other. *Immunity* 19, 391-402 (2003).
17. Marcinkiewicz, C. et al. Isolation and characterization of EMS16, a C-lectin type protein from Echis multisquamatus venom, a potent and selective inhibitor of the alpha2beta1 integrin. *Biochemistry* 39, 9857-9867. (2000).
18. Eble, J. A. & Tuckwell, D. S. The alpha2beta1 integrin inhibitor rhodocetin binds to the A-domain of the integrin alpha2 subunit proximal to the collagen-binding site. *Biochem J* 376, 77-85 (2003).
19. White, T. C. et al. The leech product saratin is a potent inhibitor of platelet integrin alpha2beta1 and von Willebrand factor binding to collagen. *FEBS J.* 274, 1481-1491 (2007).
20. Yin, H. et al. Arylamide derivatives as allosteric inhibitors of the integrin R2â1/type I collagen interaction. *Bioorg. Med. Chem. Lett.* 16, 3380-3382 (2007).
21. Choi, S. et al. Small molecule inhibitors of integrin alpha2beta1. *J. Med. Chem.* 50, 5457-5462 (2007).
22. Hagmann, W. K. et al. The discovery of sulfonylated dipeptides as potent VLA-4 antagonists. *Bioorganic & Medicinal Chemistry Letters* 11, 2709-2713 (2001).
23. Chang, L. L. et al. The discovery of small molecule carbamates as potent dual alpha4beta1/alpha4beta7 integrin antagonists. *Bioorganic & Medicinal Chemistry Letters* 12, 159-163 (2002).
24. Huryn, D. M. et al. The identification and optimization of orally efficacious, small molecule VLA-4 antagonists. *Current Topics in Medicinal Chemistry* 4, 1473-1484 (2004).
25. Xue, C. B. et al. Discovery of an orally active series of isoxazoline glycoprotein IIb/IIIa antagonists. *J. Med. Chem.* 40, 2064-2084 (1997).
26. Xue, C.-B. et al. Design, synthesis, and in vitro activities of benzamide-core glycoprotein IIb/IIIa antagonists: 2,3-diaminopropionic acid derivatives as surrogates of aspartic acid. *Bioorganic & Medicinal Chemistry* 5, 693-705 (1997).
27. Raines, R. T. 2005 Emil Thomas Kaiser Award. *Protein Sci* 15, 1219-1225 (2006).
28. Thomas, K. M., Naduthambi, D. & Zondlo, N. J. Electronic control of amide cis-trans isomerism via the aromatic-prolyl interaction. *J. Am. Chem. Soc.* 128, 2216-2217. (2006).
29. Chakrabarti, P. & Chakrabarti, S. C—H . . . O hydrogen bond involving proline residues in alpha-helices. *J. Mol. Biol.* 284, 867-873 (1998).
30. Xiao, T., Takagi, J., Coller, B. S., Wang, J.-H. & Springer, T. A. Structural basis for allostery in integrins and binding to fibrinogen-mimetic therapeutics. *Nature* 432, 59-67 (2004).
31. Luo, B.-H., Carman, C. V. & Springer, T. A. Structural basis of integrin signaling and regulation. *Annu. Rev. Immunol.* 25, 619-647 (2007).
32. Edelson, B. T. et al. Novel collectin/C1q receptor mediates mast cell activation and innate immunity. *Blood* 107, 143-150 (2006).
33. Yang, W., Shimaoka, M., Salas, A., Takagi, J. & Springer, T. A. Intersubunit signal transmission in integrins by a receptor-like interaction with a pull spring. *PNAS* 101, 2906-2911 (2004).
34. O'Toole, T. E., Katagiri, Y. & Faull, R. J. Integrin cytoplasmic domains mediate inside-out signal transduction. *J Cell Bio* 124, 1047-1059 (1994).
35. Wang, Z., Leisner, T. M. & Parise, L. V. Platelet alpha2beta1 integrin activation: contribution of ligand internalization and the alpha2-cytoplasmic domain. *Blood* 102, 1307-1315 (2003).
36. Shattil, S. J. & Newman, P. J. Integrins: dynamic scaffolds for adhesion and signaling in platelets. *Blood* 104, 1606-1615 (2004).
37. Tam, S. H., Sassoli, P. M., Jordan, R. E. & Nakada, M. T. Abciximab (ReoPro, chimeric 7E3 Fab) demonstrates equivalent affinity and functional blockade of glycoprotein IIb/IIIa and alphavbeta3 integrins. *Circulation* 98, 1085-1091 (1998).
38. Kurz, K. D., Main, B. W. & Sandusky, G. E. Rat model of arterial thrombosis induced by ferric chloride. *Thromb. Res.* 60, 269-280 (1990).
39. Farehi, P. M., Ozaki, C. K., Carmeliet, P. & Fay, W. P. Regulation of arterial thrombosis by plasminogen activator-1 in mice. *Circulation* 97, 1002-1008 (1998).
40. Kuijpers, M. J. E. et al. Role of murine integrin alpha2beta1 in thrombus stabilization and embolization: contribution of thromboxane A2. *Thromb. Haemost.* 98, 1072-1080 (2007).
41. Basani, R. B. et al. RGD-containing peptides inhibit fibrinogen binding to platelet alphaIIbbeta3 by inducing an allosteric change in the amino-terminal portion of alphaIIb. *J. Biol. Chem.* 276, 13975-13981 (2001).
42. Bellavite, P. et al. A colorimetric method for the measurement of platelet adhesion in microtiter plates. *Analytical Biochemistry* 216, 444-450 (1994).
43. Yin, H. et al. Computational design of peptides that target transmembrane helices. *Science* 315, 1817-1822 (2007).

What is claimed:

1. A compound having the formula:

wherein:
X is alkylene, N, O, S, or $SO_2$;
$R^0$ is alkylene;
$R^1$ is —NHC(=O)$R^2$;
$R^2$ is —NH(CH$_2$)aryl;
$R^3$ is H, alkyl, aryl, or aralkyl, or forms a three- to six-membered carbocyclic or heterocyclic ring together with X and the carbon atom to which $R^3$ and X are both attached;
$R^4$ and $R^5$ are each independently H or —CH$_3$;
wherein
the dashed line may represent a double bond;
if $R^4$ and $R^5$ are both H, then
X is $SO_2$; or, X is S and R³ is not H; or, X is —CH— and the dashed line represents a double bond;

and, if X is ethylidene, then one carbon atom of X, R³, and the carbon atom to which both are attached form a three- to six-membered carbocyclic or heterocyclic ring, or, X forms a fused bicycle together with Ring A;

or a stereoisomer, partial stereoisomer, pharmaceutically acceptable salt, or N-oxide thereof.

2. A composition comprising a compound according to claim 1 and a pharmaceutically acceptable carrier, diluent, or excipient.

3. A composition comprising a stereochemically enriched mixture of compounds according to claim 2.

4. The compound according to claim 1 wherein R¹ is —NHC(=O)R², X is S or O, and R³ is alkyl, aryl, or aralkyl.

5. The compound according to claim 4 wherein X is S and R⁴ and R⁵ are both H or are both —CH₃.

6. The compound according to claim 5 wherein said compound is

2-[(3-Benzenesulfonyl-2-methyl-thiazolidine-4-carbonyl)-amino]-3-(3-benzyl-ureido)-propionic acid;

2-[(3-Benzenesulfonyl-2-ethyl-thiazolidine-4-carbonyl)-amino]-3-(3-benzyl-ureido)-propionic acid;

2-[(3-Benzenesulfonyl-2-isopropyl-thiazolidine-4-carbonyl)-amino]-3-(3-benzyl-ureido)-propionic acid;

2-[(3-Benzenesulfonyl-2-tert-butyl-thiazolidine-4-carbonyl)-amino]-3-(3-benzyl-ureido)-propionic acid;

2-[(3-Benzenesulfonyl-2-phenyl-thiazolidine-4-carbonyl)-amino]-3-(3-benzyl-ureido)-propionic acid;

2-[(3-Benzenesulfonyl-2-phenethyl-thiazolidine-4-carbonyl)-amino]-3-(3-benzyl-ureido)-propionic acid;

2-[(3-Benzenesulfonyl-2,5,5-trimethyl-thiazolidine-4-carbonyl)-amino]-3-(3-benzyl-ureido)-propionic acid; or, 2-[(3-Benzenesulfonyl-2-ethyl-5,5-dimethyl-thiazolidine-4-carbonyl)-amino]-3-(3-benzyl-ureido)-propionic acid.

7. The compound according to claim 4 wherein X is O, R⁴ is H, R⁵ is —CH₃, and R³ is alkyl.

8. The compound according to claim 7 wherein the compound is 2-[(3-Benzenesulfonyl-2,5-dimethyl-thiazolidine-4-carbonyl)-amino]-3-(3-benzyl-ureido)-propionic acid.

9. The compound according to claim 1 wherein R¹ is —NHC(=O)R², R³, R⁴, and R⁵ are each H, and X is SO₂.

10. The compound according to claim 9 wherein said compound is 2-[(3-Benzenesulfonyl-1,1-dioxo-1λ⁶-thiazolidine-4-carbonyl)-amino]-3-(3-benzyl-ureido)-propionic acid.

11. The compound according to claim 1 wherein X is ethylidene, and:

one carbon atom of X, R³, and the carbon atom to which both are attached form a three- to six-membered carbocyclic or heterocyclic ring, or, X forms a fused bicycle together with Ring A.

12. The compound according to claim 11 wherein said compound is

2-[(2-Benzenesulfonyl-1,2,3,4-tetrahydro-isoquinoline-3-carbonyl)-amino]-3-(3-benzyl-ureido)-propionic acid, or 2-[(1-Benzenesulfonyl-1,2,3,4-tetrahydro-quinoline-2-carbonyl)-amino]-3-(3-benzyl-ureido)-propionic acid.

13. The compound according to claim 1 wherein X is —CH—, the dashed line represents a double bond, R¹ is —NHC(=O)R², R² is —NH(CH₂)phenyl, and R³, R⁴, and R⁵ are each H.

14. The compound according to claim 13 wherein the compound is 2-[(1-Benzenesulfonyl-2,5-dihydro-1H-pyrrole-2-carbonyl)-amino]-3-(3-benzyl-ureido)-propionic acid.

15. A method for treating at least one integrin α2β1-affected disease state or infection comprising the step of administering to a subject in need thereof a composition comprising a therapeutically effective amount of a compound having the formula:

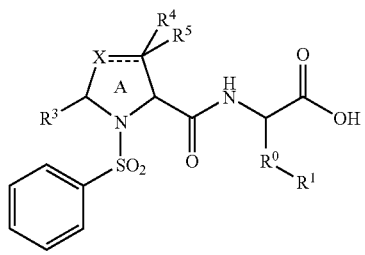

wherein:

X is alkylene, N, O, S, or SO₂;

R⁰ is alkylene;

R¹ is —NHC(=O)R²;

R² is —NH(CH₂)aryl;

R³ is H, alkyl, aryl, or aralkyl, or forms a three- to six-membered carbocyclic or heterocyclic ring together with X and the carbon atom to which R³ and X are both attached;

R⁴ and R⁵ are each independently H or —CH₃;

wherein the dashed line may represent a double bond;

if R⁴ and R⁵ are both H, then

X is SO₂; or,

X is S and R³ is not H; or,

X is —CH— and the dashed line represents a double bond;

and, if X is ethylidene, then one carbon atom of X, R³, and the carbon atom to which both are attached form a three- to six-membered carbocyclic or heterocyclic ring, or, X forms a fused bicycle together with Ring A;

or a stereoisomer, partial stereoisomer, pharmaceutically acceptable salt, or N-oxide thereof.

16. The method according to claim 15 wherein the subject is suffering from or susceptible to one or more of acute coronary syndromes, stroke, ischaemic complications of peripheral vascular disease, deep vein thrombosis (DVT), myocardial infarction, coronary artery disease, cerebrovascular disease, peripheral arterial disease, diabetes mellitus, atrial fibrillation, congestive heart failure, pulmonary embolism, and other vascular-related disorders.

17. The method according to claim 15, wherein the subject is suffering from or susceptible to one or more of human melanoma, hepatocellular carcinoma, breast cancer, lung cancer, ovarian cancer, and other cancers or cancer-related disorders.

18. The method according to claim 15, wherein the subject is suffering from or susceptible to one or more of rheumatoid arthritis, diabetic retinopathy, and other rheumatoid- or diabetes-related disorders.

19. The method according to claim 15, wherein the disease state or infection is matrix reorganization-affected, angiogenesis-affected, cell migration-, cell proliferation-, cell colonization-, or metastasis-affected, leukocyte infiltration-affected, edema-affected, or any combination thereof.

20. The method according to claim 15, where in the subject is suffering from or susceptible to viral infection.

21. The method according to claim 20, wherein said viral infection is at least partially attributable to human cytomegalovirus (HCMV), rotaviruses, Piconaviridae viruses, or related viruses.

22. The method according to claim 15 wherein said composition additionally comprises a pharmaceutically acceptable carrier, diluent, or excipient.

23. The method according to claim 15, wherein said composition comprises a stereochemically enriched mixture of compounds of the formula.

24. The method according to claim 15, wherein said subject is human.

* * * * *

UNITED STATES PATENT AND TRADEMARK OFFICE
CERTIFICATE OF CORRECTION

| | | |
|---|---|---|
| PATENT NO. | : 8,987,306 B2 | Page 1 of 1 |
| APPLICATION NO. | : 12/566162 | |
| DATED | : March 24, 2015 | |
| INVENTOR(S) | : William F. DeGrado et al. | |

It is certified that error appears in the above-identified patent and that said Letters Patent is hereby corrected as shown below:

In the specification

Column 1,
Line 13, delete "Dec. 8, 2008" and insert -- Dec. 9, 2008 --.

Lines 23-27, delete "The United States Government may have rights in the invention described herein, which was made in part with funding from the National Center for Research Resources (U.S. National Institute of Health), Grant No. UL1RR024134." and insert -- This invention was made with government support under grant number UL1RR024134 awarded by the National Institute of Health. The government has certain rights in the invention. --.

Column 7,
Line 37, delete "α2α1-affected" and insert -- α2β1-affected --.

Column 17,
Line 2, delete "tent-butyl," and insert -- tert-butyl, --.

Column 28,
Line 31, delete "β/β" and insert -- α/β --.

Signed and Sealed this
First Day of December, 2015

Michelle K. Lee
*Director of the United States Patent and Trademark Office*